(12) United States Patent
Gagnon et al.

(10) Patent No.: US 9,366,640 B2
(45) Date of Patent: Jun. 14, 2016

(54) SPARSE AND ENERGY DISCRIMINATING COLLIMATED DETECTOR ELEMENTS TO ASSIST SCATTER EVALUATION IN CT IMAGING

(71) Applicants: Kabushiki Kaisha Toshiba, Minato-ku (JP); Toshiba Medical Systems Corporation, Otawara-shi (JP)

(72) Inventors: Daniel Gagnon, Twinsburg, OH (US); Yu Zou, Naperville, IL (US); Xiaolan Wang, Buffalo Grove, IL (US)

(73) Assignees: KABUSHIKI KAISHA TOSHIBA, Minato-ku (JP); TOSHIBA MEDICAL SYSTEMS CORPORATION, Otawara-shi (JP)

( * ) Notice: Subject to any disclaimer, the term of this patent is extended or adjusted under 35 U.S.C. 154(b) by 0 days.

(21) Appl. No.: 14/134,732

(22) Filed: Dec. 19, 2013

(65) Prior Publication Data

US 2014/0105354 A1 Apr. 17, 2014

Related U.S. Application Data

(62) Division of application No. 13/526,594, filed on Jun. 19, 2012.

(51) Int. Cl.
| | | |
|---|---|---|
| *A61B 6/00* | (2006.01) | |
| *G01T 1/16* | (2006.01) | |
| *G01N 23/04* | (2006.01) | |
| *G01T 1/24* | (2006.01) | |
| *A61B 6/03* | (2006.01) | |
| *H05G 1/02* | (2006.01) | |

(52) U.S. Cl.
CPC .............. *G01N 23/046* (2013.01); *A61B 6/032* (2013.01); *A61B 6/4078* (2013.01); *A61B 6/4233* (2013.01); *A61B 6/4291* (2013.01); *A61B 6/5282* (2013.01); *G01T 1/242* (2013.01); *H05G 1/02* (2013.01)

(58) Field of Classification Search
CPC .. A61B 6/4241; A61B 6/4291; A61B 6/4233; G01T 1/1603; G01T 1/242
USPC .................... 378/98.8; 250/370.09
See application file for complete search history.

(56) References Cited

U.S. PATENT DOCUMENTS

| | | | | |
|---|---|---|---|---|
| 6,054,712 | A * | 4/2000 | Komardin et al. | ........ 250/363.06 |
| 6,568,851 | B2 * | 5/2003 | Saito | ............................. 378/207 |
| 6,587,538 | B2 * | 7/2003 | Igarashi et al. | ................. 378/19 |

(Continued)

*Primary Examiner* — David J Makiya
*Assistant Examiner* — Dani Fox
(74) *Attorney, Agent, or Firm* — Oblon, McClelland, Maier & Neustadt, L.L.P.

(57) ABSTRACT

A computed-tomography apparatus that includes a CT scanner including an X-ray source and a detector covering respective angle ranges in the axial and transaxial planes of the CT scanner. The CT detector includes first detector elements disposed on a first surface to capture incident X-ray photons emitted from the X-ray source, and second detector elements sparsely disposed on a second surface different from the first surface, the second surface being farther away from the scanner than the first surface, the second detector elements being smaller in number than the first detector elements. Each of the second detector elements is reachable only by X-ray photons originating in a small angle range around a line connecting the X-ray source and a center of the surface of the detector element, the small angle range being determined by the predetermined distance separating the first and second surfaces and a size of the detector element.

8 Claims, 20 Drawing Sheets

(56) References Cited

U.S. PATENT DOCUMENTS

| | | | |
|---|---|---|---|
| 6,762,413 B2 * | 7/2004 | Zeng | G21K 1/025 250/363.04 |
| 7,443,955 B2 | 10/2008 | Sakaguchi et al. | |
| 7,956,332 B2 | 6/2011 | Burr et al. | |
| 2008/0056432 A1 * | 3/2008 | Pack et al. | 378/4 |

* cited by examiner

SPARSE AND ENERGY DISCRIMINATING COLLIMATED DETECTOR ELEMENTS TO ASSIST SCATTER EVALUATION IN CT IMAGING

CROSS-REFERENCE TO RELATED APPLICATIONS

This application is a divisional application of U.S. application Ser. No. 13/526,594, filed Jun. 19, 2012, the entire contents of which are incorporated herein by reference.

FIELD

Embodiments disclosed herein generally relate to computed tomography (CT) imaging. In particular, embodiments disclosed herein relate to a system and an associated method to more accurately describe the contribution of scattered radiation to measured radiation so as to support an overall more accurate image reconstruction.

BACKGROUND

Radiographic imaging, in its simplest expression, is an X-ray beam traversing an object and a detector relating the overall attenuation per ray. The attenuation is derived from a comparison of the same ray with and without the presence of the object. From this conceptual definition, several steps are required to properly construct an image. For instance, the finite size of the X-ray generator, the nature and shape of the filter blocking the very low energy X-ray from the generator, the details of the geometry and characteristics of the detector, and the capacity of the acquisition system are all elements that affect how the actual reconstruction is performed. In the reconstruction, the map of the linear attenuation coefficient (LAC) of the imaged subjects is obtained from the line integrals of the LAC through an inverse Radon transform. The line integrals can be related to the logarithm of the primary intensity of the X-rays passing through the subject. However, the measured X-ray intensity on detector may include both scattering photons and primary photons. Thus, the images reconstructed from scattering, contaminated intensities may contain some scattering artifacts.

In one of many possible geometries, the X-ray source on top of the graph shown in FIG. 1 is emitting a X-ray beam forming a fan, traversing the object. While a wide range of values can exist, typically, the distance "C" is around 100 cm, "B" is around 60 cm, and "A" is around 40 cm. The principle of tomography requires that each point of the object is traversed by a collection of rays covering at least 180 degrees. Thus, the entire X-ray generator and detector assembly will rotate around the patient. Mathematical considerations show that the tomographic conditions are met when a scan of 180 degrees plus the fan angle is performed.

In addition to the details of the scanner geometry and the detector behavior, the very nature of the X-ray interaction with the matter it traverses makes the problem more complex and requires another layer of correction and compensation.

For example, scattering is one of the major sources of discrepancy between the expected attenuation behavior and the measured data from a scanner without an anti-scatter grid or with a non-perfect anti-scatter grid. The naïve assumption that all the measured photons originate directly from the X-ray source is not exactly true. X-ray photons can be diverted from their original course in a purely elastic collision (Rayleigh scattering) or in a more complex inelastic collision (Compton scattering) in which both direction and energy are affected.

The prevalence of each mode of interaction is highly dependent on the energy of the X-ray and the nature of the medium. Typically, the relative ratio follows the behavior shown in FIG. 2, which shows the attenuation coefficient as a function of energy of the X-ray for photoelectric, Compton, and Rayleigh collisions.

The angle at which the resulting Compton photon will be diverted is also highly dependent on the energy of the incident X-ray. This relationship is described by the Klein-Nishina equation and result in a progressively more forward collision as the energy of the photon increases. As shown in FIG. 3, the outer curve corresponds to a low-energy photon in which almost all angles are possible, while the inner curves shows a clear preference for the forward direction.

The end result is that the detector measures the attenuated X-ray beam plus the scattered radiation. The relationship between the measured radiation and the attenuating nature of the object is therefore more complex.

In the photon energy range of medical imaging, e.g., 20 keV-140 keV, the major interaction processes of photons and matter are the photoelectric process and Compton scattering. Rayleigh scattering has small contribution to the total attenuation. However, the Rayleigh scattering intensity on a detector is comparable to the Compton scattering intensity because Rayleigh scattering is a forward scattering in the relevant energy range.

The cross-sections (or probability) of the photoelectric process and Compton scattering are related to the effective Z of a material. For high-Z materials, the photoelectric process is dominant and fewer Compton photons are generated. For low-Z materials, the Compton process is important and more scatter photons are generated. The Rayleigh scattering process depends on the electronic structure of the atoms, molecules, and clusters of a material and cannot be described with only a few parameters. With the material information, one can estimate the strength of Compton scattering and improve the accuracy of the scatter model.

Several systems have been proposed to address scattering contamination. For example, most modern commercial scanners include an "anti-scatter" filter. This device is a collimation system exploiting the fact that all scattered photons will be diverted from their original path and will therefore enter the detector at a different angle from the photons coming directly from the X-ray tube, which is typically a small (e.g., less than one millimeter wide) point that is on the order of one meter away. Thus, as shown in FIG. 4, a series of mechanical, attenuating fins could block radiation not emanating from the source.

Two types of collimation exist. In the one-dimensional approach shown in FIG. 5, fins are arranged along the long axis (z-axis) of the scanner to prevent scattered radiation from entering the detector in the transaxial plane. It is clear, however, that radiation can enter the detector in this design if the radiation stays in an axial plane.

It is indeed possible to build a two-dimensional array of fins that provide shielding for scattered radiation for all planes, as shown in FIG. 6. Of course, construction of such a device is not without its own complexity and cost, especially when considering that the detector elements are typically 1 mm×1 mm, sometimes even smaller. It is also to be realized that this filter, due to the fact that a finite amount of material is necessary to block the scattered radiation, will also block some of the desired, unscattered, primary beam. With strong requirements to minimize the amount of radiation required to produce a desired image, blocking "good" photons at the detector is generally not a good strategy. For this reason, the one-dimensional filter is generally preferred, but requires additional correction since, by definition, it will allow some amount of scattered radiation in the axial planes.

One of a multiple of ways to address this problem is to use a forward scatter model with a polychromatic X-ray source. In such a model, the scatter intensities are expressed as a combination of Compton scattering and Rayleigh scattering. In the scatter model, each of the scattering intensity terms is modeled as a two-dimensional convolution of a forward function and a Gaussian kernel in each view. The forward function is related to the primary intensities that can be obtained by subtracting the scatter intensities from the measured total intensities. Polychromatic factors for Rayleigh scattering and Compton scattering are included in the respective forward functions. These polychromatic factors depend on the rays through effective energy of the spectrum for the specific ray. Scatter cross sections depend on photon energy and each ray has its effective energy due to the bowtie filter for a polychromatic source. Thus, the effective energy is related to the cross sections to account for the polychromatic effect. The Gaussian kernels are derived from the differential cross-sections of Rayleigh scattering and Compton scattering. Due to the forward nature of Rayleigh scattering in the energy range of medical imaging, it is described by a narrow Gaussian kernel. The Compton process is related to the wide kernel. The effect of a one-dimensional anti-scatter filter can also be included in the kernels. For each view, an iterative procedure is adopted to obtain the primary intensities from the measured total intensities.

The disadvantage of conventional CT systems is that the reduction of scattered radiation is made at the expense of the general dose efficiency of the system, and that the compromise approach using a one-dimensional filter still relies on a series of assumptions that are sometimes not clearly met.

For example, FIGS. 7A-7E show the CT numbers for various materials as a function of the slice number for an ACT phantom. Compared with the true value, the CT numbers from the scatter correction model for air, water, and polyethylene are accurate, but the CT numbers of bone and acrylic illustrate the scatter over-correction. The over-correction can be attributed to the relatively high Z feature of bone and acrylic. High Z materials generate fewer scatter photons, but the model assumes relatively low Z material (water), which has high scatter Compton probability.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DETAILED DESCRIPTION

Figure 1:
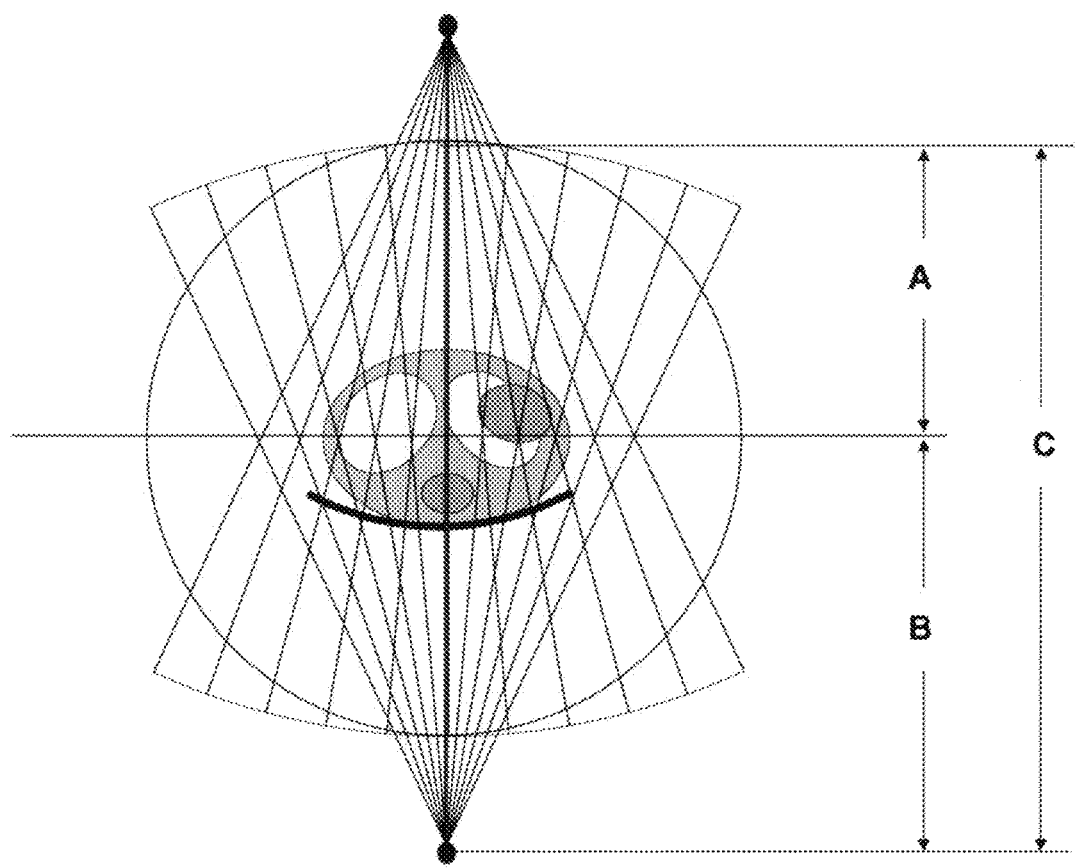
FIG. 1 illustrates a conventional X-ray source emitting a X-ray beam forming a fan, traversing an object.
Figure 2:
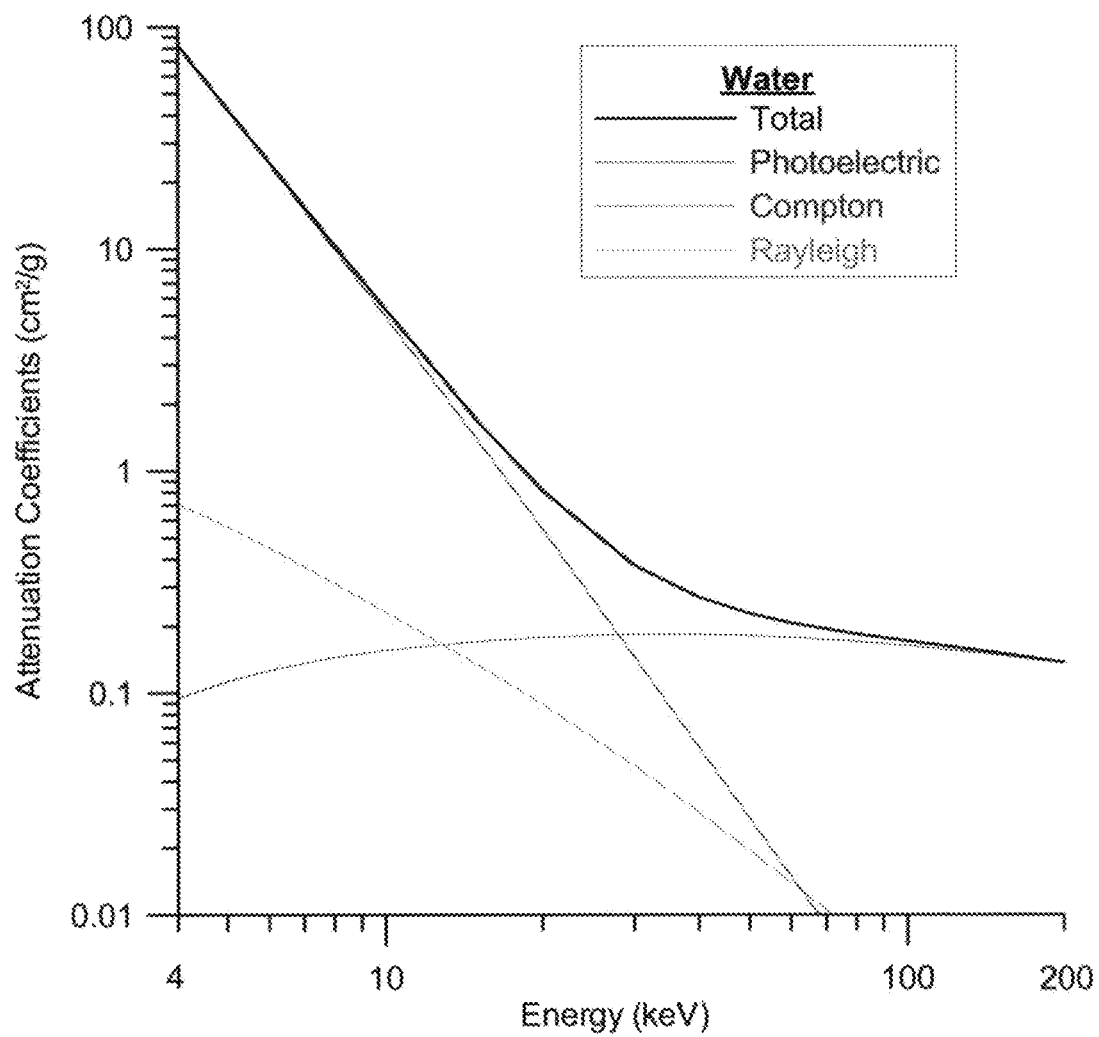
FIG. 2 illustrates the X-ray attenuation coefficient of water as a function of energy of the X-ray for photoelectric, Compton, and Rayleigh collisions.
Figure 3:
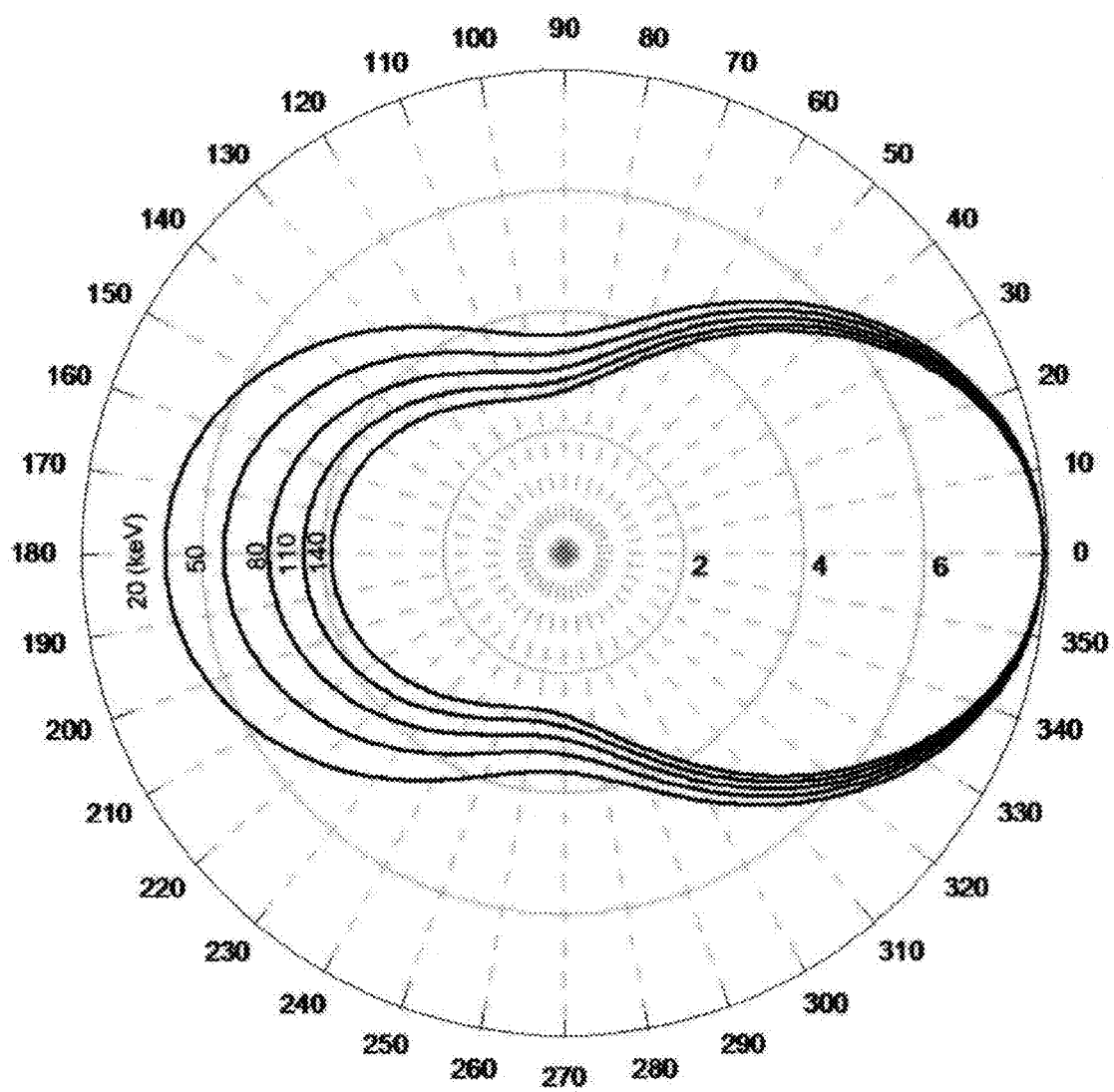
FIG. 3 illustrates the angle at which a Compton photon will be diverted as a function of the energy of the incident X-ray, indicating a progressively more forward collision as the energy of the photon increases.
Figure 4:
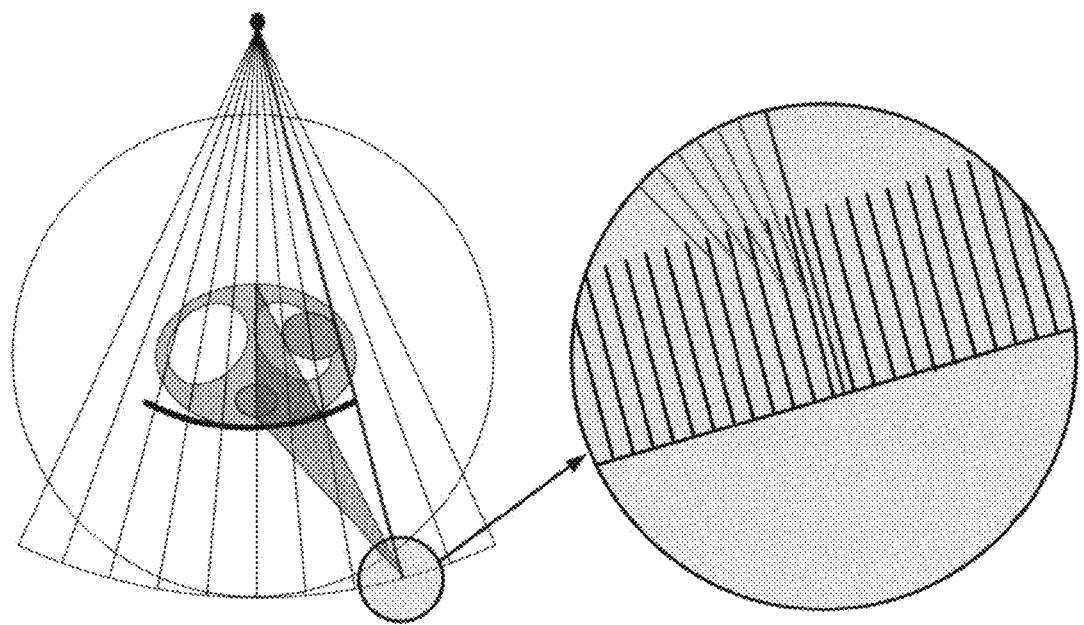
FIG. 4 illustrates an "anti-scatter" filter having a series of mechanical, attenuating fins that block radiation not emanating from the source.
Figure 5:
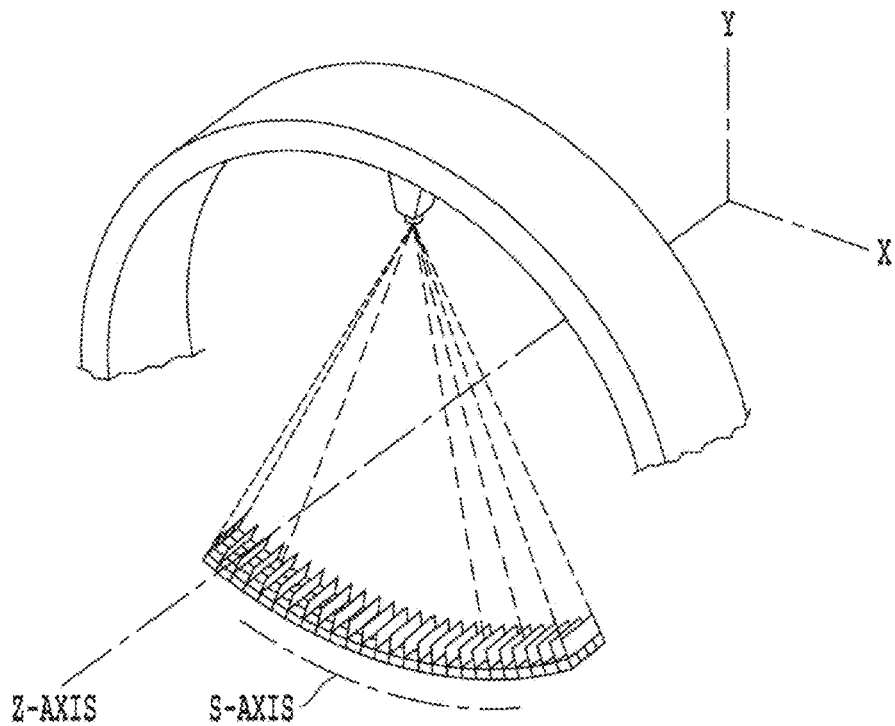
FIG. 5 illustrates one-dimensional collimation in which fins are arranged along the long axis (z-axis) of the scanner to prevent scattered radiation from entering the detector in the transaxial plane.
Figure 6:
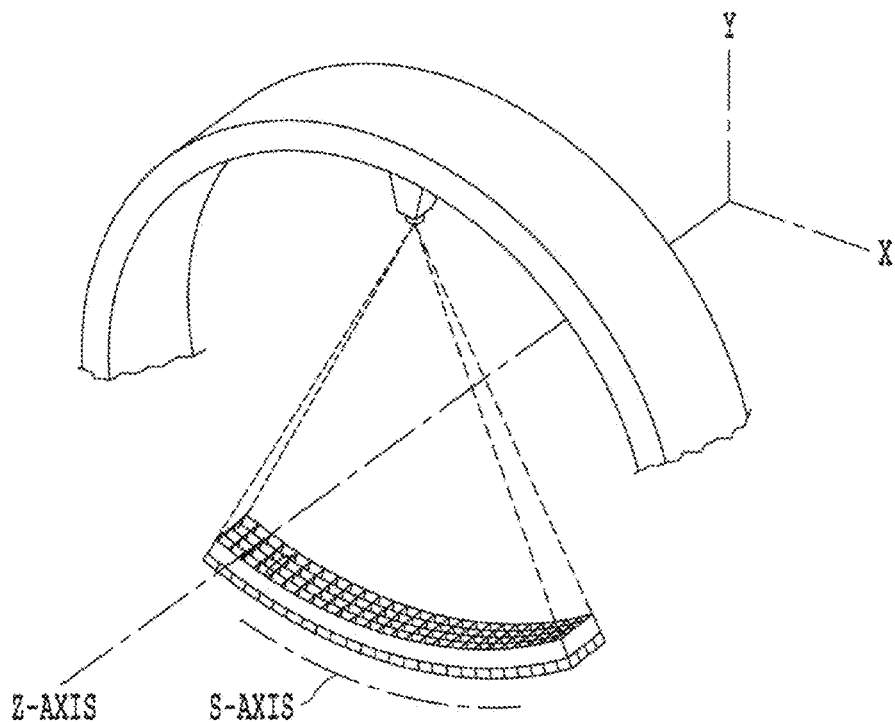
FIG. 6 illustrates a two-dimensional array of fins that provide shielding for scattered radiation for all planes.
Figure 7A:
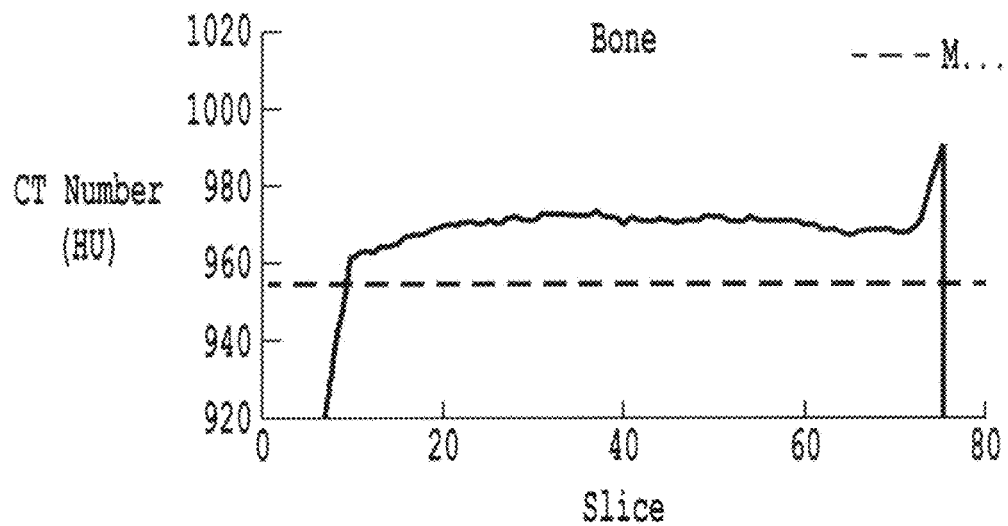
FIGS. 7A-7E illustrate CT numbers for various materials as a function of the slice number for an ACT phantom.
Figure 7B:
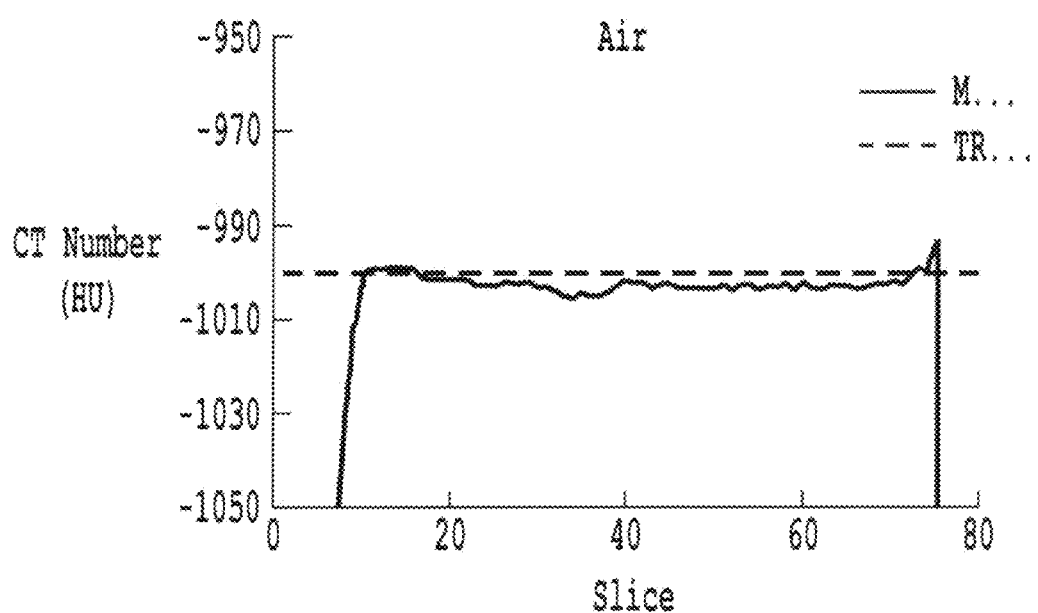
Figure 7C:
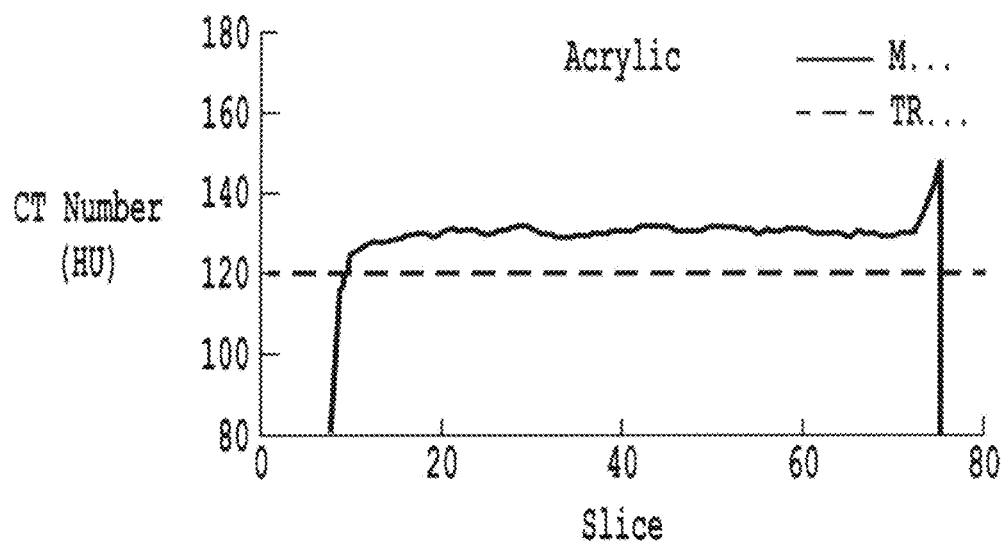
Figure 7D:
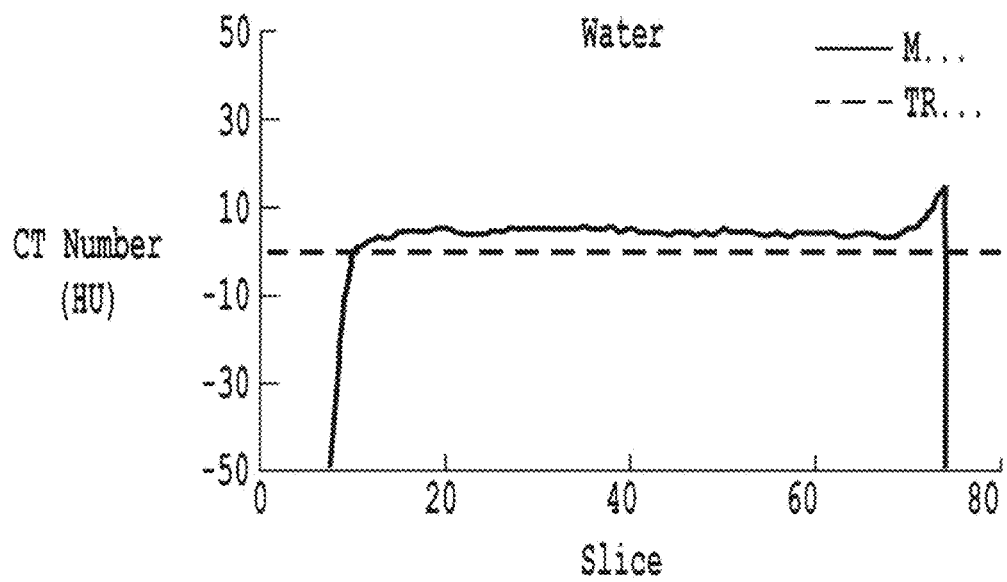
Figure 7E:
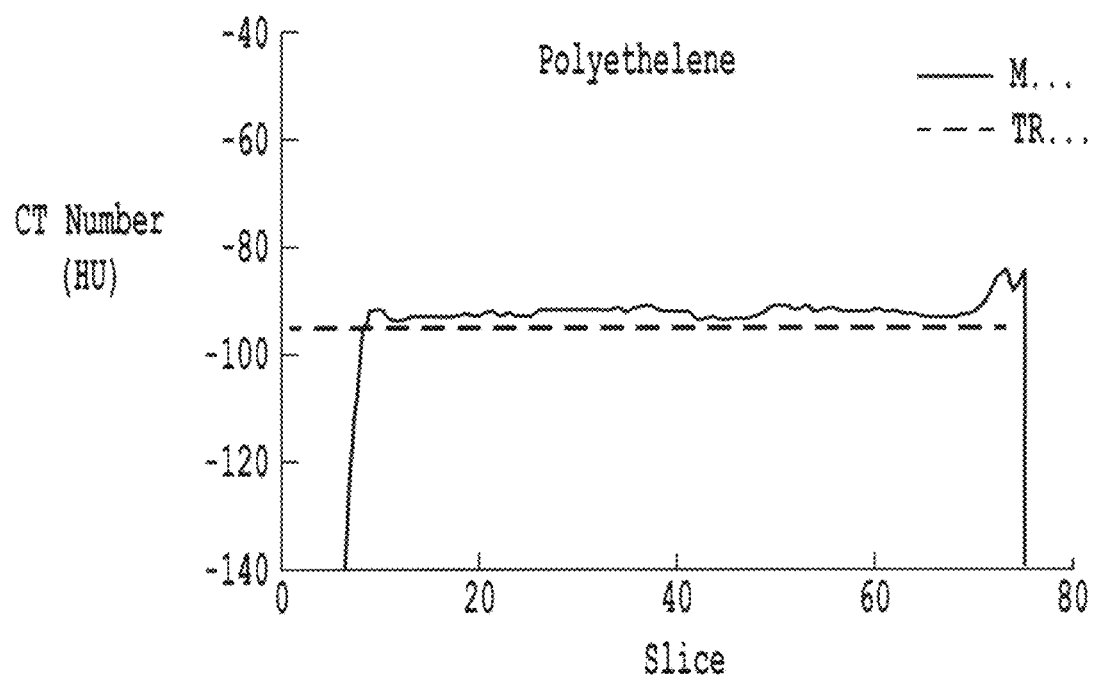

Embodiments described herein are directed to a new system and method providing better information on the scatter content of a given CT acquisition.

In one embodiment, there is provided a computed-tomography (CT) detector covering respective angle ranges in the axial and transaxial planes of a CT scanner having an X-ray source, the CT detector comprising: (1) a first plurality of detector elements disposed on a first surface to capture incident X-ray photons emitted from the X-ray source; and (2) a second plurality of detector elements sparsely disposed on a second surface different from the first surface, the second surface being farther away from the X-ray source than the first surface by a predetermined distance, the second plurality of detector elements being smaller in number than the first plurality of detector elements. Further, each detector element of the second plurality of detector elements is reachable only by X-ray photons originating in a small angle range around a line connecting the X-ray source and a center of the surface of the detector element, the small angle range being determined by the predetermined distance separating the first and second surfaces and a size of the detector element. In one embodiment, each of the second plurality of detector elements is an energy-discriminating (photon-counting) detector element, while each of the first plurality of detector elements is a conventional detector element. However, any combination of photon-counting and conventional elements can be used for both the first and second plurality of elements.

In another embodiment, there is provided a computed-tomography (CT) detector covering respective angle ranges in the axial and transaxial planes of a CT scanner having an X-ray source, the CT detector comprising: (1) a plurality of detector elements disposed on a first surface to capture incident X-ray photons emitted from the X-ray source; and (2) a plurality of collimators sparsely disposed on the first surface, each collimator being associated with one of the plurality of detector elements and having a predetermined height, wherein the plurality of collimators are smaller in number than the plurality of detector elements. Further, each detector element having a corresponding collimator is reachable only by X-ray photons originating in a small angle range around a line connecting the X-ray source and a center of the surface of the detector element, the small angle range being determined by the predetermined height of the corresponding collimator.

In another embodiment, there is provided a computed-tomography (CT) apparatus, comprising: (1) a CT scanner including an X-ray source; and (2) a detector covering respective angle ranges in the axial and transaxial planes of the CT scanner. The CT detector includes (a) a first plurality of detector elements disposed on a first surface to capture incident X-ray photons emitted from the X-ray source; and (b) a second plurality of detector elements sparsely disposed on a second surface different from the first surface, the second surface being farther away from the X-ray source than the first surface by a predetermined distance, the second plurality of detector elements being smaller in number than the first plurality of detector elements, wherein each detector element of the second plurality of detector elements is reachable only by X-ray photons originating in a small angle range around a line connecting the X-ray source and a center of the surface of the detector element, the small angle range being determined by the predetermined distance separating the first and second surfaces and a size of the detector element.

In another embodiment, the X-ray source is a fast kV-switching X-ray source having an uncertain voltage waveform and an uncertain current waveform, and the CT apparatus further includes a processor configured to estimate parameters defining both the voltage waveform and the current waveform based on data acquired from the plurality of detector elements and a spectrum model.

Further, in another embodiment, the CT apparatus further includes a processor configured to estimate, for each element of the second plurality of detector elements, a total intensity at the element by averaging intensity values at neighboring elements within the first plurality of detector elements, and to determine a scatter intensity at the element by subtracting a measured primary intensity at the element from the estimated total intensity at the element.

In another embodiment, there is provided a computed-tomography (CT) apparatus, comprising: (1) a CT scanner including an X-ray source; and (2) a detector covering respective angle ranges in the axial and transaxial planes of the CT scanner. The CT detector includes (a) a first plurality of detector elements disposed on a first surface to capture incident X-ray photons emitted from the X-ray source; and (b) a second plurality of detector elements sparsely disposed on a second surface different from the first surface, the second surface being farther away from the X-ray source than the first surface by a predetermined distance, the second plurality of detector elements being smaller in number than the first plurality of detector elements, and each of the second plurality of detector elements being configured to detect a plurality of X-ray intensity levels, wherein each detector element of the second plurality of detector elements is reachable only by X-ray photons originating in a small angle range around a line connecting the X-ray source and a center of the surface of the detector element, the small angle range being determined by the predetermined distance separating the first and second surfaces and a size of the detector element.

The CT apparatus further includes a processor configured to estimate, for each element of the second plurality of detector elements, a total intensity at the element by averaging intensity values at neighboring elements within the first plurality of detector elements, and to determine a scatter intensity at the element by subtracting a measured primary intensity at the element from the estimated total intensity at the element.

In a further embodiment, the processor is configured to: (1) average, for each element of the second plurality of detector elements, the measured intensity at the element over multiple views, to obtained an average primary intensity at each element of the second plurality of detector elements, (2) estimate the scatter intensity at each element of the second plurality of detector elements by subtracting the average primary intensity from the estimated total intensity at the element, (3) estimate a scatter intensity at each element of the first plurality of detector elements by interpolation using the estimated scatter intensity at each element of the second plurality of detector elements, and (4) calculate a primary intensity at each element of the first plurality of detector elements by subtracting the estimated scatter intensity at each element from the measured intensity at each element.

In another embodiment, the processor is further configured to estimate the scatter intensity at each element of the first plurality of detector elements by interpolation, using the determined scatter intensity at each of the second plurality of detector elements.

Further, in another embodiment, the processor is configured to: (1) estimate a scatter intensity and a primary intensity for each element of the first and second plurality of detector elements using a scatter model, (2) compare, for each of the plurality of second detector elements, a measured primary intensity with the estimated primary intensity, (3) average, for each of the plurality of second detector elements, the measured primary intensity over multiple views, (4) perform dual energy decomposition based on the averaged primary intensities to obtain a photoelectric component and a Compton component, (5) modify a forward function based on the obtained Compton component, (6) recalculate the scatter intensity and the primary intensity for each element of the first and second plurality of detector elements, and (6) repeat the modify and recalculate steps until the estimated primary intensity agrees with the measured primary intensity, for each of the plurality of second detector elements.

In another embodiment, each of the second plurality of detector elements is an energy-discriminating detector element, and the CT apparatus further comprises (1) a first data acquisition system configured to collect information regarding received incident X-ray photons at the first plurality of detector elements using a first predetermined sample time interval, and (2) a second data acquisition system configured to collect information regarding received incident X-ray photons at the second plurality of detector elements using a second predetermined sample time interval different from the first predetermined sample time interval. In one embodiment, the second predetermined sample time interval is longer than the first predetermined time interval.

In another embodiment, the second data acquisition system is configured to collect the information for each of the second plurality of detector elements over a larger angular range than is collected by the second data acquisition system for the first plurality of detector elements so that the second predetermined sample time interval is longer than the first predetermined sample time interval.

In another embodiment there is provided a computed-tomography (CT) apparatus, comprising: (1) a CT scanner including a fast kV-switching X-ray source having an uncertain voltage waveform and an uncertain current waveform; (2) a detector covering respective angle ranges in axial and transaxial planes of the CT scanner, the CT detector including a plurality of energy-discriminating detector elements; and (3) a processor configured to estimate parameters defining both the voltage waveform and the current waveform based on data acquired from the plurality of energy-discriminating detector elements and a spectrum model.

In one embodiment, the processor is configured to (1) determine an initial estimate for the parameters, (2) define a cost function that is based on (a) measured photon numbers for a plurality of energy bins, which are obtained from the data acquired from the plurality of energy-discriminating detector elements, and (b) calculated photon numbers that are calculated based on the spectrum model and linear attenuation coefficients, (3) calculate partial derivatives of the cost function with respect to each of the parameters, and (4) determine an updated estimate for the parameters based on the calculated partial derivatives of the cost function.

In another embodiment, the processor is further configured to (1) determine a difference between the updated estimate for the parameters and the initial estimate for the parameters, (2) determine whether the determined difference between the updated estimate and the initial estimate is less than a predetermined threshold, and (3) repeat the steps of calculating the partial derivatives of the cost function, determining an updated estimate for the parameters, and determining a difference between the updated estimate and a previous estimate until the determined difference is less than the predetermined threshold.

Further, in another embodiment there is provided a method of determining a voltage waveform and a current waveform for a CT apparatus having a CT scanner including a fast kV-switching X-ray source, and a detector including a plurality of energy-discriminating detector elements, the method comprising: (1) acquiring data from the plurality of energy-discriminating detector elements; and (2) estimating parameters defining both the voltage waveform and the current waveform based on the acquired data and a spectrum model, wherein the estimating step includes (i) determining an initial estimate for the parameters, (ii) defining a cost function that is based on (1) measured photon numbers for a plurality of energy bins, which are obtained from the data acquired from the plurality of energy-discriminating detector elements, and (2) calculated photon numbers that are calculated based on the spectrum model and linear attenuation coefficients, (iii) calculating partial derivatives of the cost function with respect to each of the parameters, and (iv) determining an updated estimate for the parameters based on the calculated partial derivatives of the cost function.

In another embodiment, the estimating step further comprises: (1) determining a difference between the updated estimate for the parameters and the initial estimate for the parameters; (2) determining whether the determined difference between the updated estimate and the initial estimate is less than a predetermined threshold; and (3) repeating the steps of calculating the partial derivatives of the cost function, determining an updated estimate for the parameters, and determining a difference between the updated estimate and a previous estimate until the determined difference is less than the predetermined threshold.

Figure 8A:
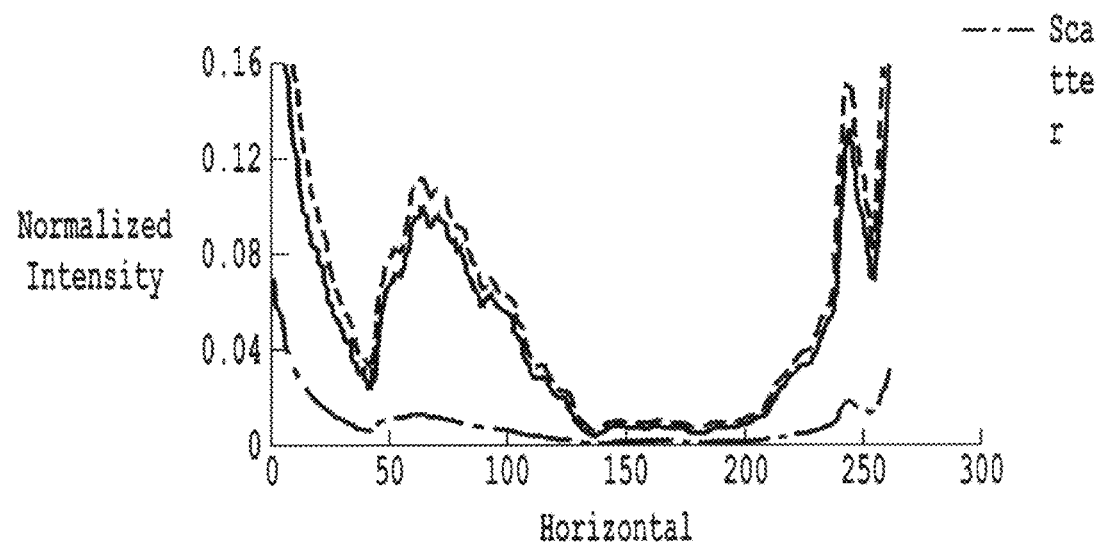
FIGS. 8A and 8B illustrate an example of the spatial variation of the scatter intensity compared to the primary intensity.
Figure 8B:
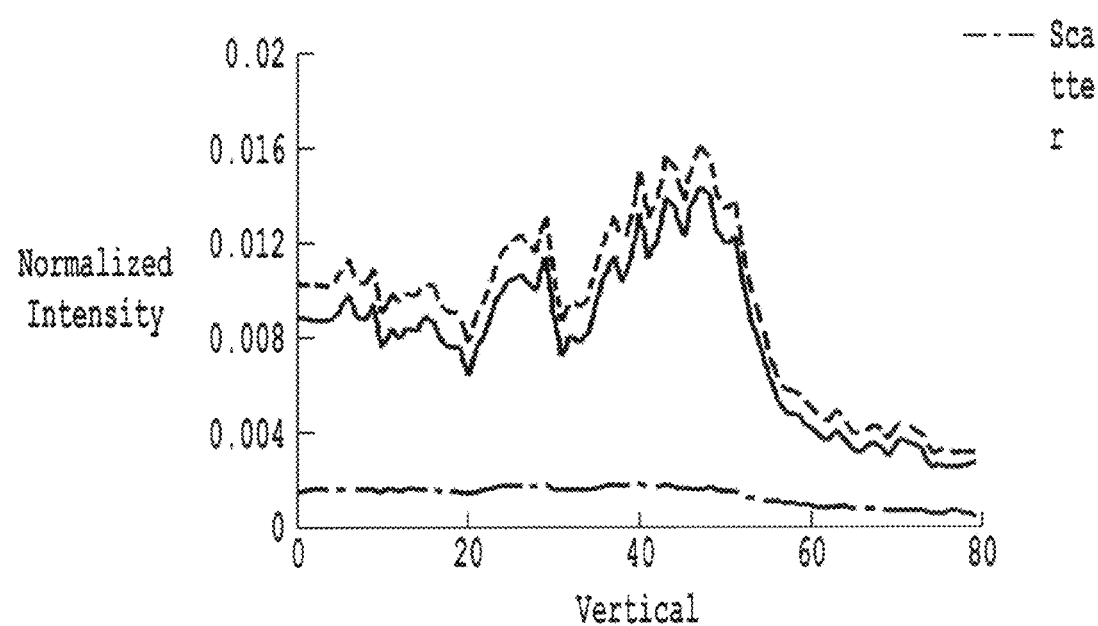

Turning now to the drawings, FIGS. 8A and 8B illustrate that the spatial variation of the scatter intensity is much lower than the primary intensity. FIGS. 8A and 8B are examples from a clinical scan. Due to the low-frequency nature of scatter intensities, sparse spatial sampling is possible.

The first embodiment is based on a proper model describing the distribution of scatter and the knowledge that the distribution has a much lower frequency that the object under investigation. Accordingly, the first embodiment includes a system with a sparse distribution of collimation tubes, e.g., every $16^{th}$ detector element, as shown in FIG. 9, providing very accurate sampling points of the object without scatter that act as constraints to the scatter model for the entire object.

In this embodiment, the combination of sparse sampling and a model that can be used to estimate scatter will leave large regions unobstructed to collect more useful direct photons. Of course, FIG. 9 can be generalized to three dimensions in which the collimation tubes restrict the photon paths in three dimensions. In this geometry, the tubes will be oriented directly towards the X-ray source so that the 2D fan geometry extrapolated to the 3D cone geometry results in a "spherical" arrangement for the collimation tubes.

Figure 9:
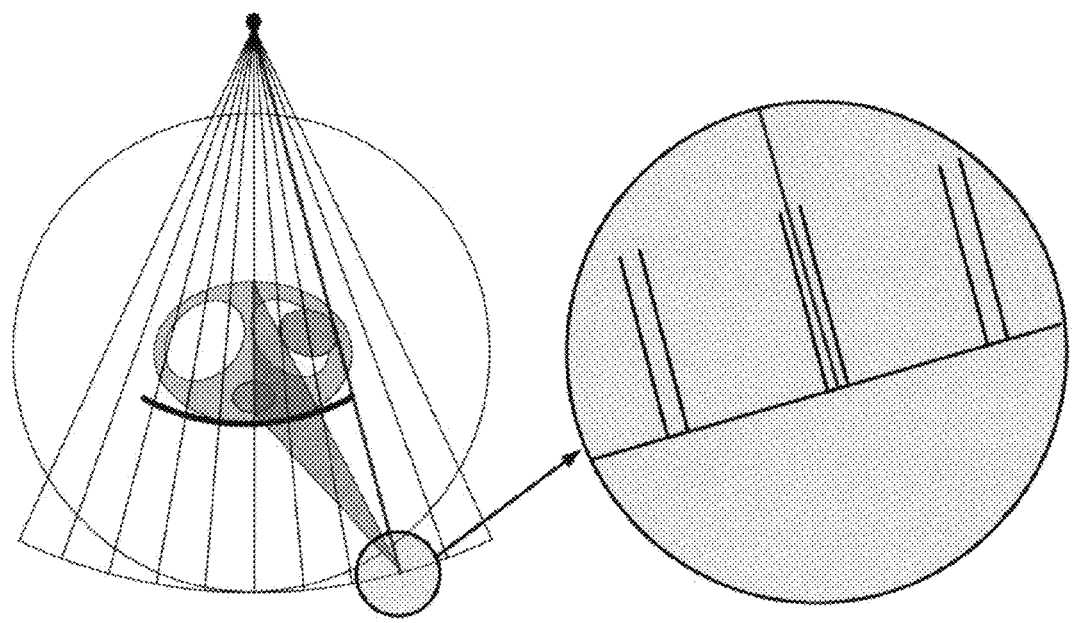
FIG. 9 illustrates an embodiment in which a detector array has a sparse distribution of collimation tubes.
Figure 10:
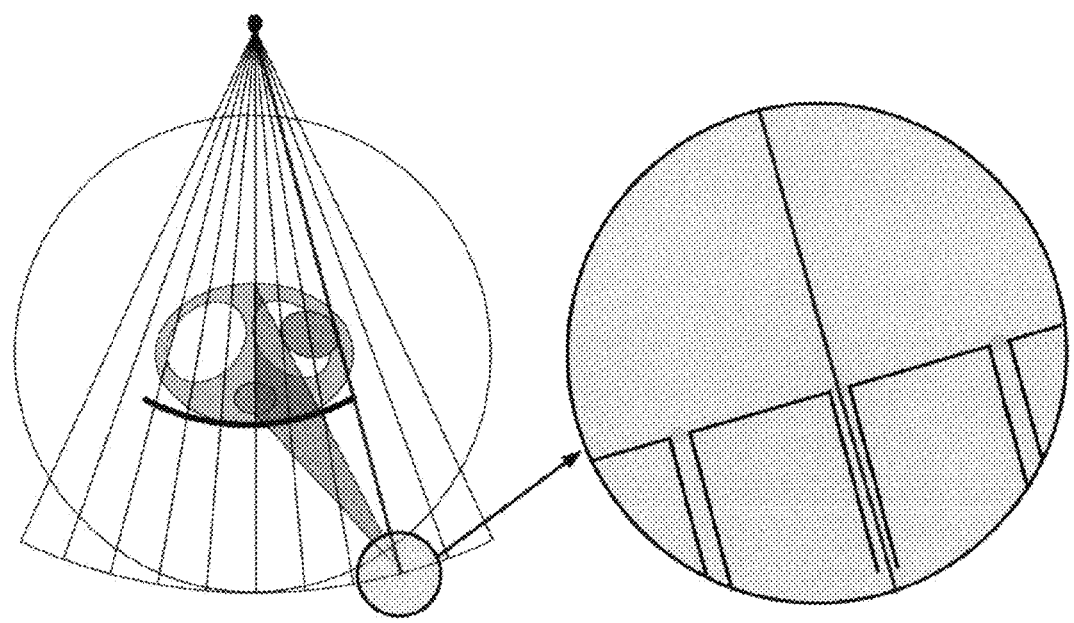
FIG. 10 illustrates a second embodiment in which a detector array has a sparse distribution of collimation tubes inside the detector.

In an alternative embodiment, the collimation tubes accomplish the same results when they are "inside" the detector, as shown in FIG. 10, as opposed to being "outside" the detector, as shown in FIG. 9. The advantages of the inside tubes are clear, e.g., eliminating "shadowing" of the scattered radiation that could make the estimation more complex and improving geometric efficiency of the detector. The inside tubes also reduce the dose waste when primary photons are blocked and prevented from reaching the non-collimated detector elements.

Figure 18:
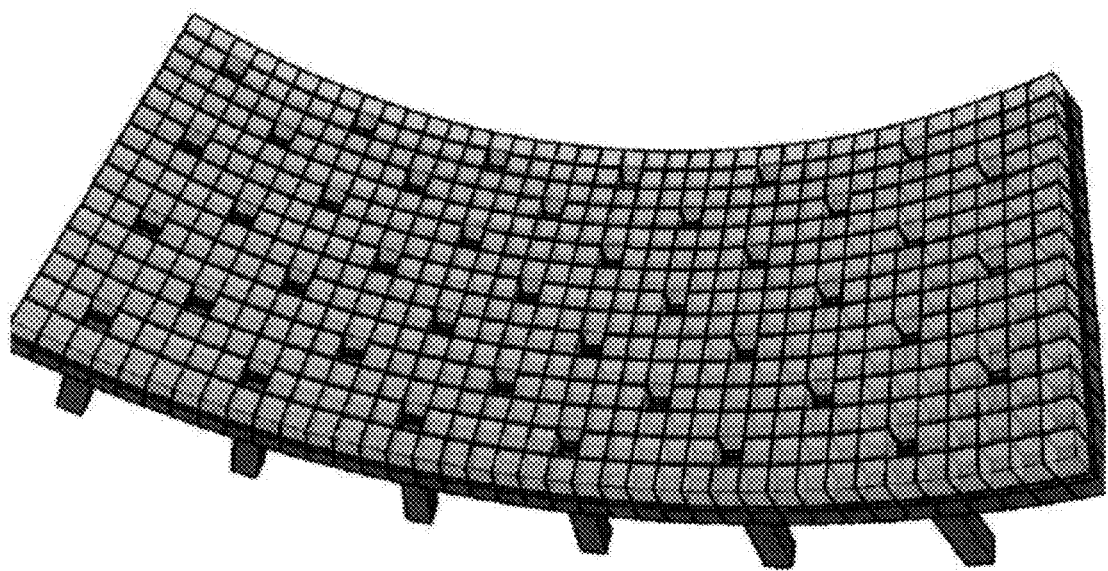
FIG. 18 is a diagram of a CT detector having a series of sparse collimation tunnels distributed across the detector, wherein either a conventional or photon-counting detector element is arranged at the bottom of each tunnel so as to collect scatter-free events.

Similar to the detector of FIG. 10, FIG. 18 illustrates a detector having a series of sparse collimation tunnels distributed across the detector, wherein either a conventional or photon-counting detector element is arranged at the bottom of each tunnel so as to collect substantially scatter-free events.

Figure 11:
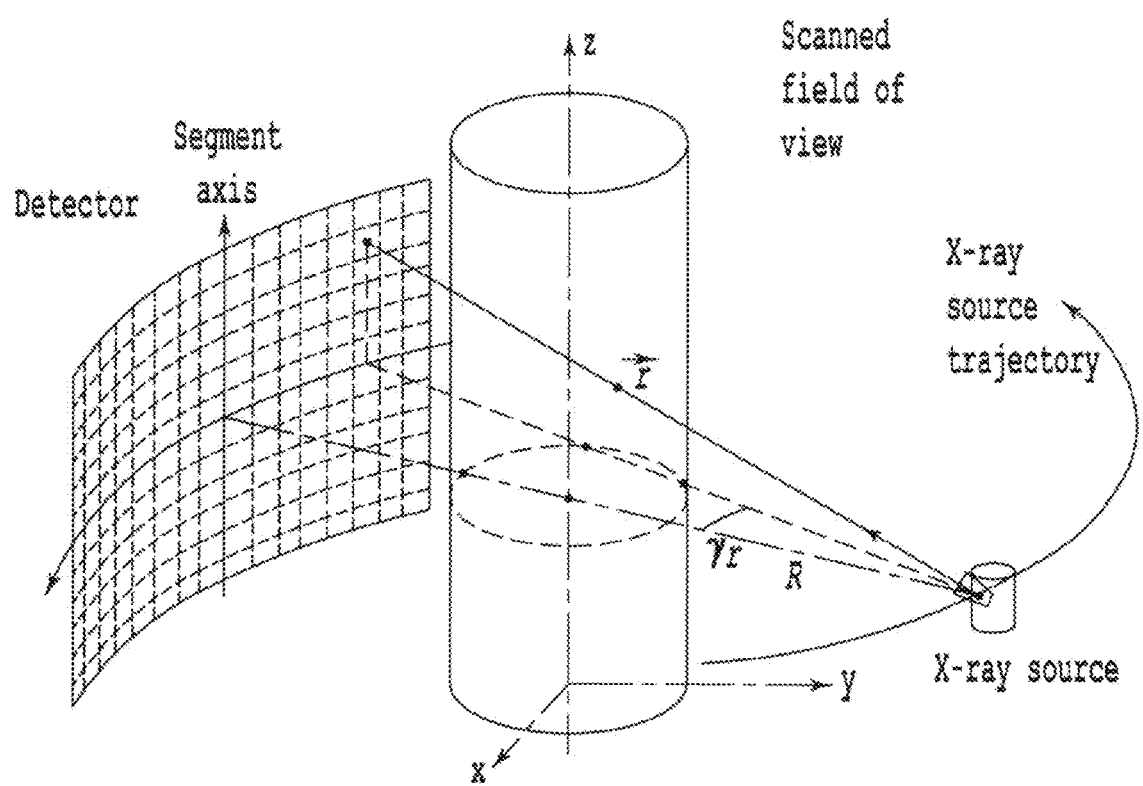
FIG. 11 illustrates the geometry of an X-ray scanner including an X-ray source and a detector array.

In three dimensions, each collimation hole or tunnel has to be exactly parallel to the vector "r" shown in FIG. 11.

Figure 12:
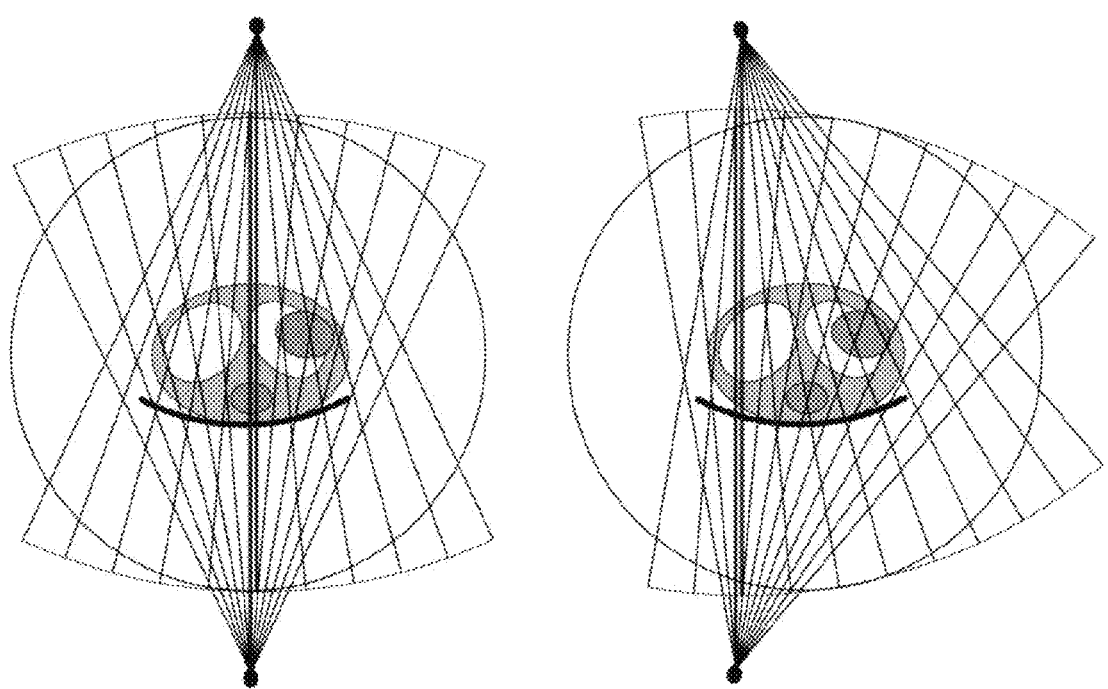
FIGS. 12 and 13 illustrate the production of redundant samples due to the sampling performed by the rotation of the X-ray tube.
Figure 13:
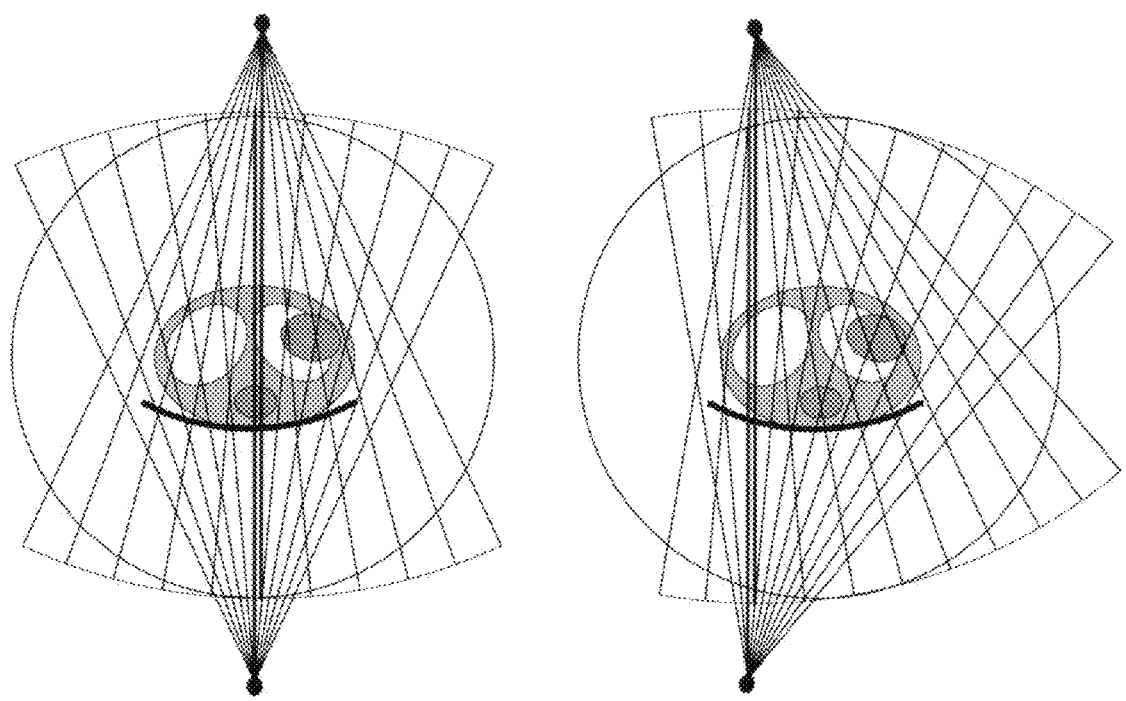

Additionally, the sampling performed by the rotation of the X-ray tube produces redundant samples, every 180 degrees for the central ray, and at some other angle for any given other ray, as indicated in FIGS. 12 and 13. This principle is exploited in the "quarter pixel shift" which, by purposely positioning the pixel off its theoretical place, the sampling is increased as the normally redundant sample would then be shifted by half a pixel.

Using the same principle, at least in the central plane for circular orbit, the density of collimation tunnels can be doubled when appropriately disposed on the detector, offering a higher density of constraint points for full 360 degree orbits, and a sparser array of points for normal imaging.

One potential limitation of this approach is that, due to the existence of the collimating tubes, detectors under the tube will collect fewer photons than those on the rest of the detector surface. Therefore, those "scatter-free" data suffer from a higher statistic noise, which can degrade the efficiency of the scatter compensation scheme. To address this limitation, one solution is to temporally smooth the data by summing or averaging over multiple projection views. Due to the very small increment angle of one projection view (usually <0.5°) on a modern commercial CT scanner, the spatially blurring resulting from this smoothing can be offset by the significantly improved statistic. For example, summing two projection views increases the signal-to-noise ratio by more than 40% (70% for three views). As a result, the overall image quality is improved.

Further, temporal smoothing is more important when a more advanced X-ray detector with energy discriminating capability, e.g., a multi-threshold photon counting detector or a spectrometer, is used under the collimating tube. The additional spectral information provided by such detectors improves the efficiency of scatter compensation. But since such detectors only measure X-ray photons in a certain energy range, the data tend to be noisier than those from a conventional X-ray detector in which all photons, regardless of energy, are collected. Thus, it is desirable to smooth the scatter-free data to an acceptable noise level before being applied for scatter correction on the full dataset.

Using the sparsely sampled primary intensity values, the scatter intensity can be estimated directly or the data can be incorporated into the scatter correction model so as to improve the scatter estimation.

In the direct estimate approach, at each detector element where the primary intensity is sampled, the total intensity at the element is estimated by averaging the values at neighboring elements. Then, the scatter intensity at the element can be obtained by subtracting the measured primary intensity from the estimated total intensity. Since the scatter intensity varies slowly, the scatter intensity at any detector element can be estimated through interpolation.

Figure 14:
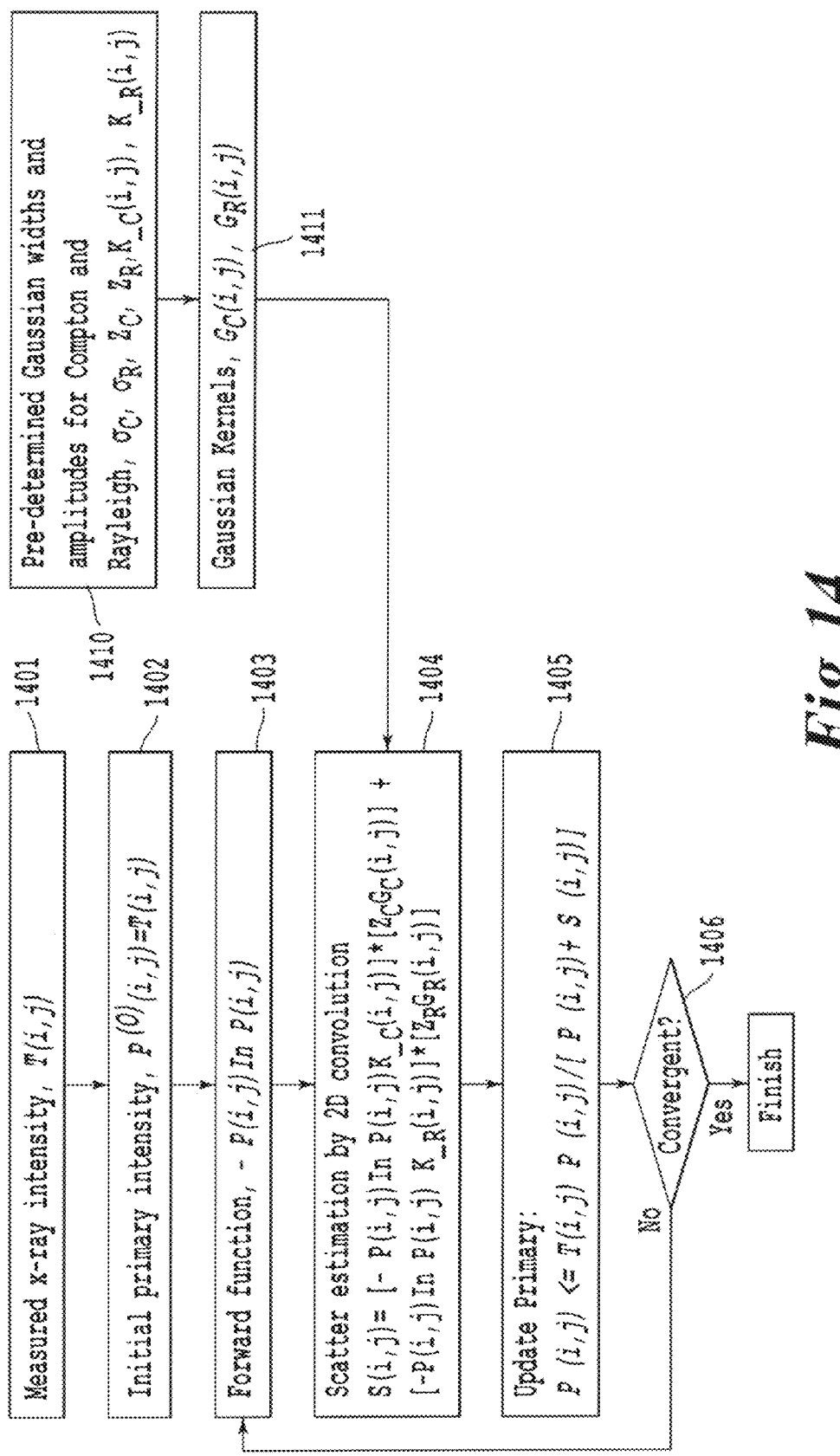
FIG. 14 is a flowchart illustrating a conventional scatter correction approach.

A conventional scatter correction method is shown in the flowchart of FIG. 14.

In step 1401, the measured X-ray intensity $T(i,j)$ is obtained, where $T(i,j)$ represents the total measured intensity at detector element $(i,j)$.

In step 1402, an initial primary intensity, $P^{(0)}(i,j)=T(i,j)$ is determined, where $P(i,j)$ represents the primary intensity at detector $(i,j)$ element.

In step 1403, the forward function, $-P(i,j)\ln P(i,j)$ is calculated.

In step 1404, scatter estimation is performed by 2D convolution as follows:

$$S(i,j)=[-P(i,j)\ln P(i,j)K\_C(i,j)]*[Z_C G_C(i,j)]+[-P(i,j)\ln P(i,j)K\_R(i,j)]*[Z_R G_R(i,j)].$$

In step 1405, the primary intensities are updated as follows:

$$P(i,j)=T(i,j)P(i,j)/[P(i,j)+S(i,j)].$$

In step 1406, a check is made to see if the sum of the differences between two iterations over all detector elements is small or the iteration number has reached the maximum. If so, the process is finished. Otherwise, the process proceeds to step 1403.

In step 1410, the Gaussian widths and amplitudes for Compton and Rayleigh scattering, $\sigma_C$, $\sigma_R$, $Z_C$, $Z_R$, $K\_C(i,j)$, $K\_R(i,j)$ are predetermined.

In step 1411, the Gaussian kernels $G_C(i,j)$, $G_R(i,j)$ are determined.

The tunnel-collimator, scatter-correction model method of correcting for scatter, which is discussed in more detail below, includes the following steps.

First, a scatter model is applied to the total intensity data to estimate the scatter intensity and the primary intensity. Second, the estimated primary intensity is compared with the sparsely measured primary intensity to identify regions where the difference is large. Next, the scatter and primary intensities are recalculated with the modified forward function to improve the accuracy of scatter estimation.

Figure 15:
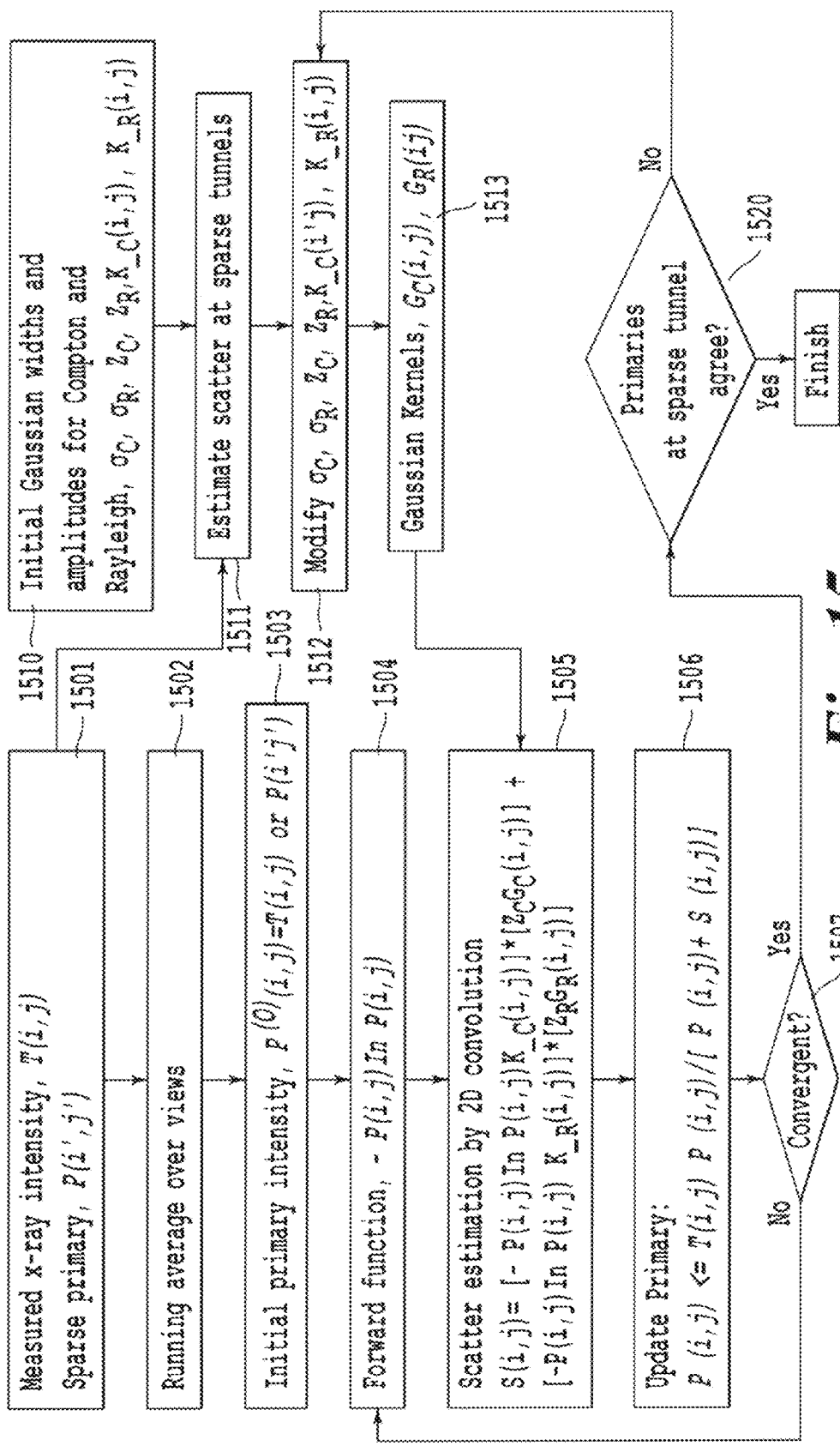
FIG. 15 is a flowchart illustrating a scatter correction method using sparse tunnel collimators.

FIG. 15 illustrates a scatter correction method when sparse tunnel collimators are used.

In step 1501, the measured X-ray intensity $T(i,j)$ and the sparse primary intensity $P(i',j')$ is obtained. For $T(i,j)$, i and j range over all values except those at the collimated elements.

In step 1502, a running average over several views of intensity is performed.

In step 1503, an initial primary intensity is determined as follows: $P^{(0)}(i,j)=T(i,j)$ or $P(i',j')$.

In step 1504, the forward function, $-P(i,j)\ln P(i,j)$ is calculated.

In step 1505, scatter estimation is performed by 2D convolution as follows:

$$S(i,j)=[-P(i,j)\ln P(i,j)K\_C(i,j)]*[Z_C G_C(i,j)]+[-P(i,j)\ln P(i,j)K\_R(i,j)]*[Z_R G_R(i,j)].$$

In step 1506, the primary intensities are updated as follows for the regions in which the measured primary values disagree with the estimated primary:

$$P(i,j)=T(i,j)P(i,j)/[P(i,j)+S(i,j)].$$

In step 1507, a check is made to see if the sum of the differences between two iterations over all detector elements is small or the iteration number has reached the maximum. If so, the process is finished. Otherwise, the process proceeds to step 1504.

In step 1510, initial values for the Gaussian widths and amplitudes for Compton and Rayleigh scattering, $\sigma_C$, $\sigma_R$, $Z_C$, $Z_R$, $K\_C(i,j)$, $K\_R(i,j)$ are determined.

In step 1511, the scatter at the sparse tunnel locations is estimated using the measured intensities $T(i,j)$ and the sparse primary intensity $P(i',j')$ obtained in step 1501.

In step 1512, $\sigma_C$, $\sigma_R$, $Z_C$, $Z_R$, $K\_C(i,j)$, $K\_R(i,j)$ are modified based on the estimated scatter determined in step 1511. The predetermined parameters are from water. The scatter intensities for water and a real object can be used to adjust the parameters.

In step 1513, the Gaussian kernels $G_C(i,j)$, $G_R(i,j)$ are determined.

Figure 16A:
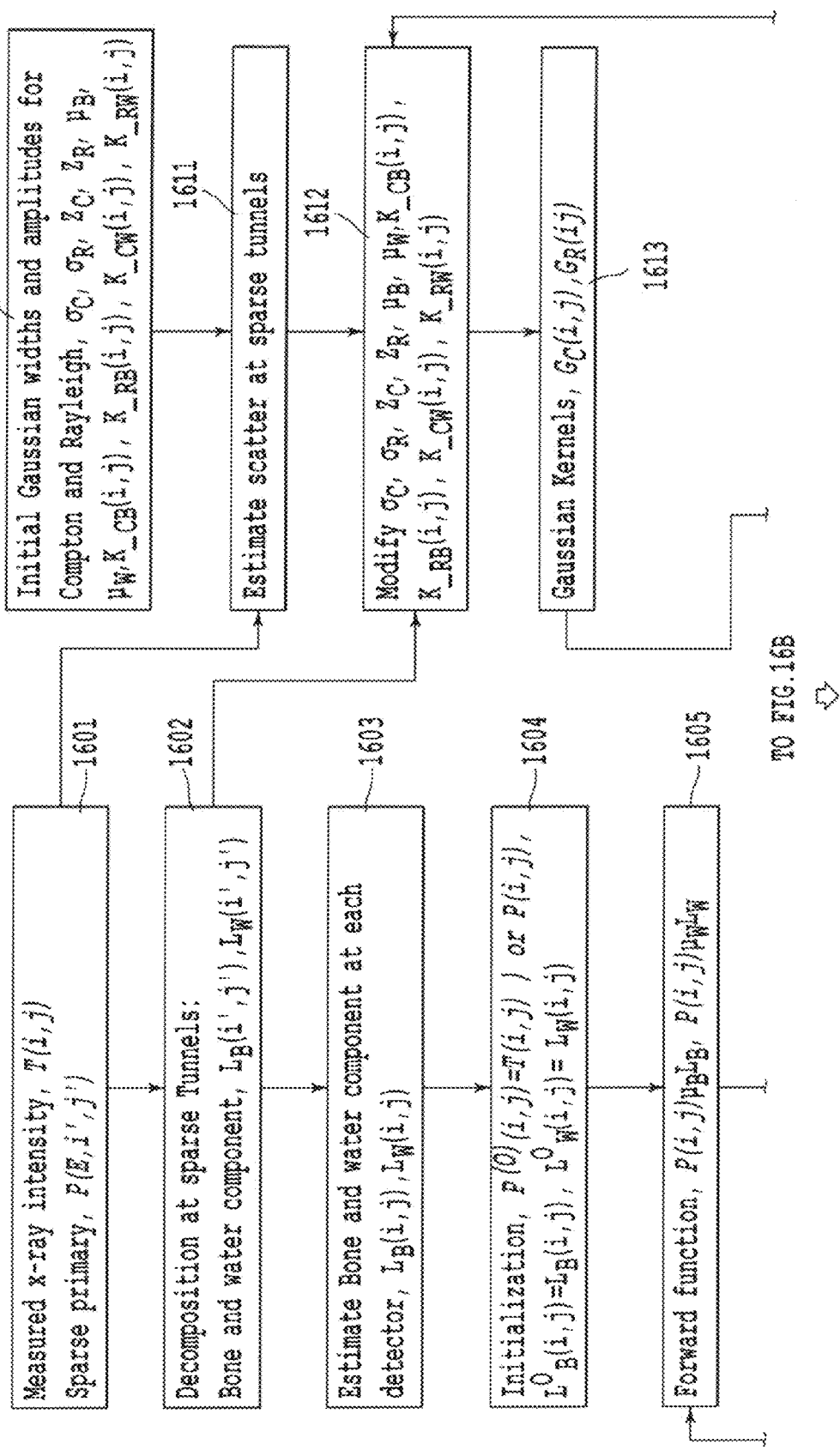
FIGS. 16A and 16B are a flowchart illustrating a scatter correction method using sparse tunnel collimators with photon-counting detector elements.
Figure 16B:
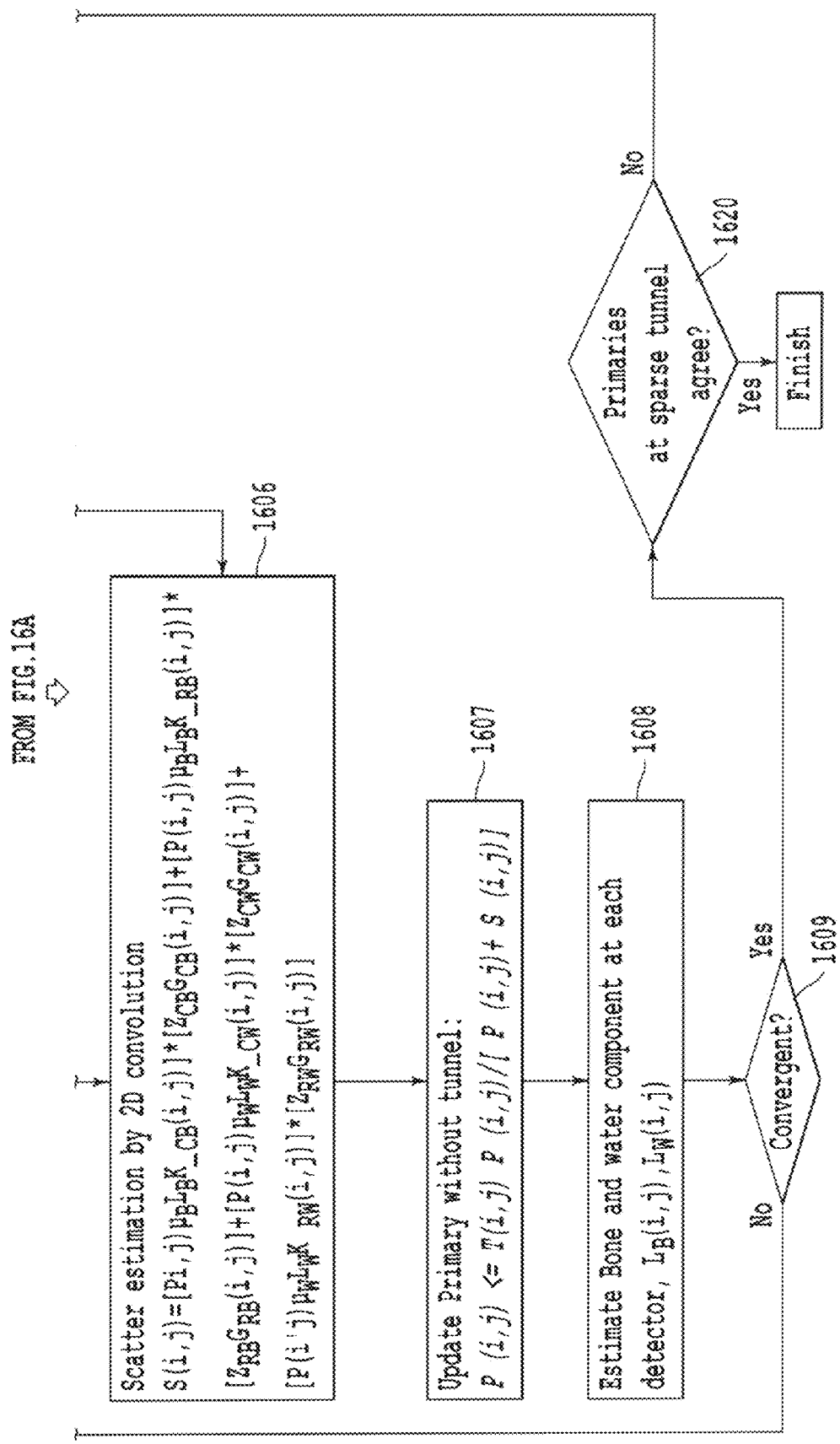

FIGS. 16A and 16B illustrate a scatter correction method when sparse tunnel collimators are used with photon-counting detector elements.

In step 1601, the measured X-ray intensity $T(i,j)$ and the sparse primary intensity $P(E,i',j')$ is obtained. For $T(i,j)$, i and j range over all values except those at the collimated elements.

In step 1602, decomposition for bone and water components, $L_B(i',j')$, $L_W(i',j')$, is performed for the sparse tunnel locations.

In step 1603, the bone and water components at each detector element, $L_B(i,j)$, $L_W(i,j)$, are estimated.

In step 1604, an initial primary intensity is determined as follows, $P^{(0)}(i,j)=T(i,j)$ or $P(i',j'))$, and initial bone and water components are $L^0{}_B(i,j)=L_B(i,j)$, $L^{(0)}{}_W(i,j)=L_W(i,j)$ are determined.

In step 1605, the forward functions, $P(i,j)\mu_B L_B$, $P(i,j)\mu_W$ are calculated.

In step 1606, scatter estimation is performed by 2D convolution as follows:

$$S(i,j)=[P(i,j)\mu_B L_B K\_{CB}(i,j)]*[Z_{CB}G_{CB}(i,j)]+[P(i,j)\mu_B L_B K\_{RB}(i,j)]*[Z_{RB}G_{RB}(i,j)]+[P(i,j)\mu_W L_W K\_{CW}(i,j)]*[Z_{CW}G_{CW}(i,j)]+[P(i,j)\mu_W L_W K\_{RW}(i,j)]*[Z_{RW}G_{RW}(i,j)].$$

In step 1607, the primary intensities, excluding the tunnel locations, are updated as follows for the regions in which the measured primary value disagrees with estimated primary value:

$$P(i,j)=T(i,j)P(i,j)/[P(i,j)+S(i,j)].$$

In step 1608, the bone and water components at each detector, $L_B(i,j)$, $L_W(i,j)$, are estimated.

In step 1609, a check is made to see if the sum of the differences between two iterations over all detector elements is small or the iteration number has reached the maximum. If so, the process proceeds to step 1620. Otherwise, the process proceeds back to step 1605.

In step 1620, a check is made to determine whether the estimated primary intensities (sum over all energy bins) at the sparse tunnel locations agree with the measured primary intensities. If yes, the process finishes, otherwise the process proceeds to step 1612.

In step 1610, initial values for the Gaussian widths and amplitudes for Compton and Rayleigh scattering, $\sigma_C$, $\sigma_R$, $Z_C$, $Z_R$, $\mu_B$, $\mu_W$, $K\_{CB}(i,j)$, $K\_{RB}(i,j)$, $K\_{CW}(i,j)$, $K\_{RW}(i,j)$ are determined.

In step 1611, the scatter at the sparse tunnel locations is estimated using the measured intensities $T(i,j)$ and the sparse primary intensity $P(E,i',j')$ obtained in step 1601.

In step 1612, $\sigma_C$, $\sigma_R$, $Z_C$, $Z_R$, $\mu_B$, $\mu_W$, $K\_{CB}(i,j)$, $K\_{RB}(i,j)$, $K\_{CW}(i,j)$, $K\_{RW}(i,j)$ are modified based on the estimated scatter determined in step 1611. The predetermined parameters are from water. The scatter intensities for water and a real object can be used to adjust the parameters.

In step 1613, the Gaussian kernels $G_C(i,j)$, $G_R(i,j)$ are determined.

The sparse spectral response from the same apparatus can also be used to stabilize possible errors or variation in a dual-energy system using a fast kV switching method. In such a system, energy information on the X-ray beam traversing the object (patient) is obtained, not by recording the energy component of each one of the X-ray photons forming the beam, but by changing the characteristic of the beam itself by rapidly alternating the voltage of the X-ray tube. Using this approach, and a synchronization with the detection system, useful spectral information on the object is obtained. A limitation of this approach is that the engineering requirements to rapidly alternate bias voltages (often in excess of hundreds of kilo-volts) are not trivial, and an imperfect waveform transitioning from one voltage to the next will limit the quality of the information. In one embodiment, the sparsely collimated energy discriminating detector elements are used to directly measure the variation in the spectrum in time. However, this process can also be performed without the use of sparse collimators.

For example, assume a fast kV-switching X-ray source with an uncertainty in the waveform of the voltage and current. This uncertainty will cause an error in simulated spectra and, accordingly, in the beam-hardening tables. With the measurements from the sparse photon-counting detectors, the uncertainty in the waveform can be eliminated to improve the accuracy of the dual-energy decomposition.

For example, assume the waveform can be parameterized by N parameters. Including the basis lengths of L1 and L2, there are N+2 unknowns. If the photon-counting detector has N+2 energy windows, the N+2 unknowns can be found at each sparse ray. Since the N waveform parameters are only dependent on the view, but not the rays in the view, the N waveform parameters are applied to the rays measured with conventional detectors. The N waveform parameters from different photon counting detectors are averaged to improve the accuracy. When the number of unknowns in the waveform is larger than the number of energy windows in the photon-counting detector, the measured data from multiple photon counting detectors must be combined to solve for the N unknowns (e.g., assume each photon-counting detector has at least three energy windows). This configuration can be considered as a hybrid CT system. The counting rate issue will not be important compared to a CT apparatus with a pure photon-counting detector. The accuracy of dual energy decomposition should be higher than that in fast kV-switching DECT, and the 2D anti-scatter grid should be unnecessary because of the sparse tunnels.

In one embodiment, the waveform parameters in fast kV switching with photon-counting detectors can be determined using the method set forth in FIG. 19 and described in detail below.

Assume that $t_0$, $t_1$, and $t_2$ represent three time points and that $N_1(E_k)$ and $N_2(E_k)$ indicate the photon numbers for energy bin k obtained with a photon counting detector from $t_0$ to $t_1$ and $t_1$ to $t_2$, respectively. Further, assume that the current waveform between $t_0$ and $t_2$ can be written as, $$i(t)=f_i(a_1,a_2,\ldots a_N;t), t\in[t_0,t_2]. \quad (1)$$

The voltage waveform between $t_0$ and $t_2$ can be written as, $$V(t)=f_V(b_1,b_2,\ldots b_M;t), t\in[t_0,t_2]. \quad (2)$$

The waveform parameters $(a_1, a_2, \ldots a_N)$ and $(b_1, b_2, \ldots b_M)$ can be determined by the measured photon numbers.

The incident spectrum during $t_0$ to $t_1$ can be expressed as, $$S_1(E)=\int_{t_0}^{t_1} dt\, i(t) S(V(t),E). \quad (3)$$

where $S(V,E)$ represents a spectrum for a specific voltage V. The spectrum can be calculated with a spectrum model.

The incident spectrum during $t_1$ to $t_2$ can be expressed as, $$S_2(E)=\int_{t_1}^{t_2} dt\, i(t) S(V(t),E). \quad (4)$$

The measured counts can be related to the spectra by:

$$N_1(E_k) = \int_{E_{k-1}}^{E_k} dE\, S_1(E) \exp\left[-\sum_{j=1}^{J} \mu_j(E) L_j\right], k \in [1, K]. \quad (5a)$$

$$N_2(E_k) = \int_{E_{k-1}}^{E_k} dE\, S_2(E) \exp\left[-\sum_{j=1}^{J} \mu_j(E) L_j\right], k \in [1, K]. \quad (5b)$$

where $\mu_j(E)$ indicates a linear attenuation coefficient of basis material j and $L_j$ is the corresponding length in a specific ray path. Here we have 2K equations and M+N+J unknown parameters. If 2K≥M+N+J, equations (5a) and (5b) determine the M+N+J unknown parameters.

For 2K<M+N+J, we need more than one photon counting detector to determine the waveform parameters. Assume we have $N_D$ photon counting detectors. We will have $2KN_D$ independent measurements that give $2KN_D$ equations. The total unknowns are $JN_D+M+N$. Note that waveforms are independent of ray paths; all the rays correspond to the same set of waveform parameters. Assuming path length $L_j$ is different for each ray, the measurements are independent.

By design, the energy bin number K can be larger than the number J of basis materials. We have $2KN_D \geq JN_D+M+N$ if $N_D$ is large enough. Then, the waveform parameters $(a_1, a_2, \ldots a_N)$ and $(b_1, b_2, \ldots b_M)$ can be obtained by solving the family of equations (5a) and (5b) as follows.

First, define a cost function:

$$\psi(\vec{a}, \vec{L}) = \sum_{l} \sum_{k=1}^{K} \left[ (N_1^{(m)}(E_k, l) - N_1(E_k, l))^2 + (N_2^{(m)}(E_k, l) - N_2(E_k, l))^2 \right]. \quad (6)$$

wherein $\vec{a}=(a_1, a_2, \ldots a_N, b_1, b_2, \ldots b_M)$, $\vec{L}=(L_j(l))$, l indicates different rays or detectors, and $N_1^{(m)}(E_k, l)$ represents the measured data.

By minimizing the cost function, we can find $\vec{a}$ and $\vec{L}$, namely, $$(\vec{a}, \vec{L}) = \mathrm{argmin} \quad (7)$$

$$\left\{ \sum_l \sum_{k=1}^K \left[ (N_1^{(m)}(E_k, l) - N_1(E_k, l))^2 + (N_2^{(m)}(E_k, l) - N_2(E_k, l))^2 \right] \right\}.$$

More specifically, the minimization can be performed using an iterative process:

1. Initial estimate of $(a_1, a_2, \ldots a_N, b_1, b_2, \ldots b_M)$ and $L_j(l)$.
2. Calculate partial derivatives of the cost function.
3. Update $(a_1, a_2, \ldots a_N, b_1, b_2, \ldots b_M)$ and $L_j(l)$ according to the derivative.
4. Repeat 2-3 until convergence or a predetermined maximum number of iterations.

Figure 19:
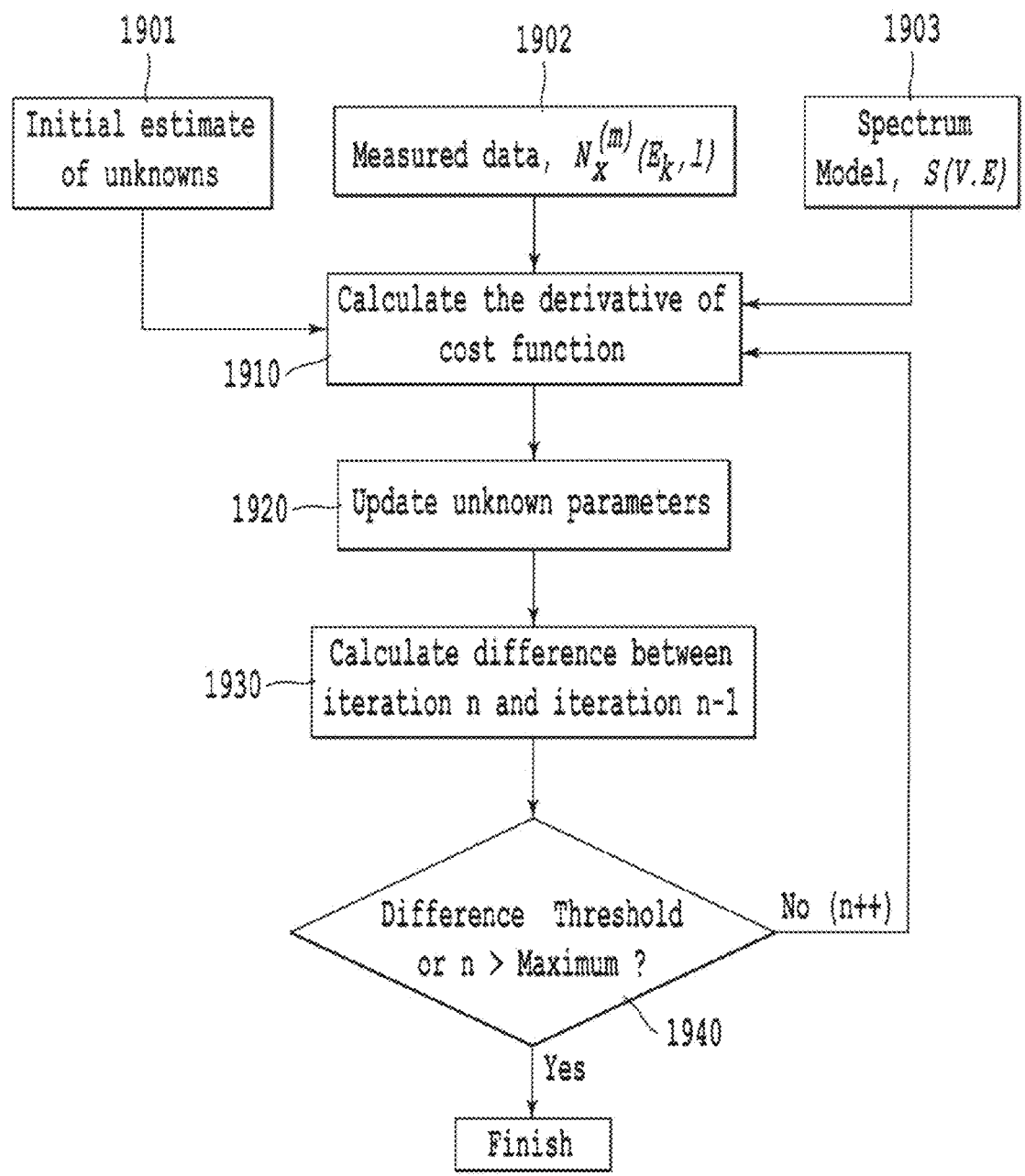
FIG. 19 is a flowchart of a method to determine waveform parameters in fast kV switching using photon-counting detectors.

FIG. 19 is a flowchart illustrating this process in more detail.

In step 1901, an initial estimate of the waveform parameters $(a_1, a_2, \ldots a_N, b_1, b_2, \ldots b_M)$ and $L_j(l)$ is determined.

In step 1902, the measured data $N_x^{(m)}(E_k, l)$ detected by the photon-counting detectors is acquired, wherein $E_k$ is an energy level and l indicates different rays or detectors.

In step 1903, the spectrum model, S(V,E) is provided.

In step 1910, estimates of the partial derivatives of the cost function with respect to the unknown (waveform) parameters is calculated.

In step 1920, the waveform parameters are updated using the partial derivatives calculated in step 1910. The waveform parameters can be updated using various known methods such as Newton's method, steepest descent, conjugate gradient, etc.

In step 1930, the difference between the waveform parameters at iteration n and iteration n−1 is calculated.

In step 1940, a check is performed to determine whether the difference calculated in step 1930 is below a preset threshold or if the number of iterations n exceeds a predetermined value. If the answer to either check is yes, the method terminates. Otherwise, the process proceeds back to step 1910.

Other numerical methods of minimizing the cost function can be used and are within the scope of this embodiment.

Steps 1901-1940 can be implemented by a processor or other specialized hardware as part of a CT apparatus.

The embodiments disclosed herein allow for a more accurate and precise scatter correction while improving the detection efficiency of the detector by removing all other filters. This improved detection efficiency of direct photons is used to improve image quality and/or reduce the required dose to the patient.

In the current forward scatter model, the material information is contained only in the forward function, but not in the Gaussian kernel. The Gaussian kernel is derived from the scatter probability, which is dependent on the material. For example, the scatter probability of bones is much lower than that of soft tissues. The current Gaussian kernel is for water, to represent soft tissues in the patient. Thus, in the bone region, scatter overcorrection can be observed. With the sparse photon-counting detector disclosed herein, the material information is obtained from the spectral data and is incorporated into the scatter model to improve accuracy.

In a third embodiment, a CT apparatus includes a detector assembly having sparse collimated energy-discriminating detector elements and non-collimated detector elements, wherein the sparse collimated energy-discriminating elements acquire data over a larger angular rotation (or sample time interval/resolution) of the detector assembly than data is acquired for the non-collimated detector elements. Each of the collimated detector elements is an energy-discriminating detector element.

In particular, the CT apparatus includes a first data acquisition system configured to collect information regarding received incident X-ray photons at the non-collimated detector elements using a first predetermined sample time interval, and a second data acquisition system configured to collect information regarding received incident X-ray photons at the collimated detector elements using a second predetermined sample time interval different from the first predetermined sample time interval. In this embodiment, the non-collimated detector elements can include conventional integrating elements or photon-counting detector elements. In a modern CT, the combination of X-ray source and detector are rotating in a fixed geometry at speeds of 200 or even 300 rotations per minute. The data acquisition readout system is set to extract the value of each detector element at a fixed, pre-determined angular (or time) interval. In this embodiment, it is straightforward to establish different time/angular intervals for each detector element.

Figure 17:
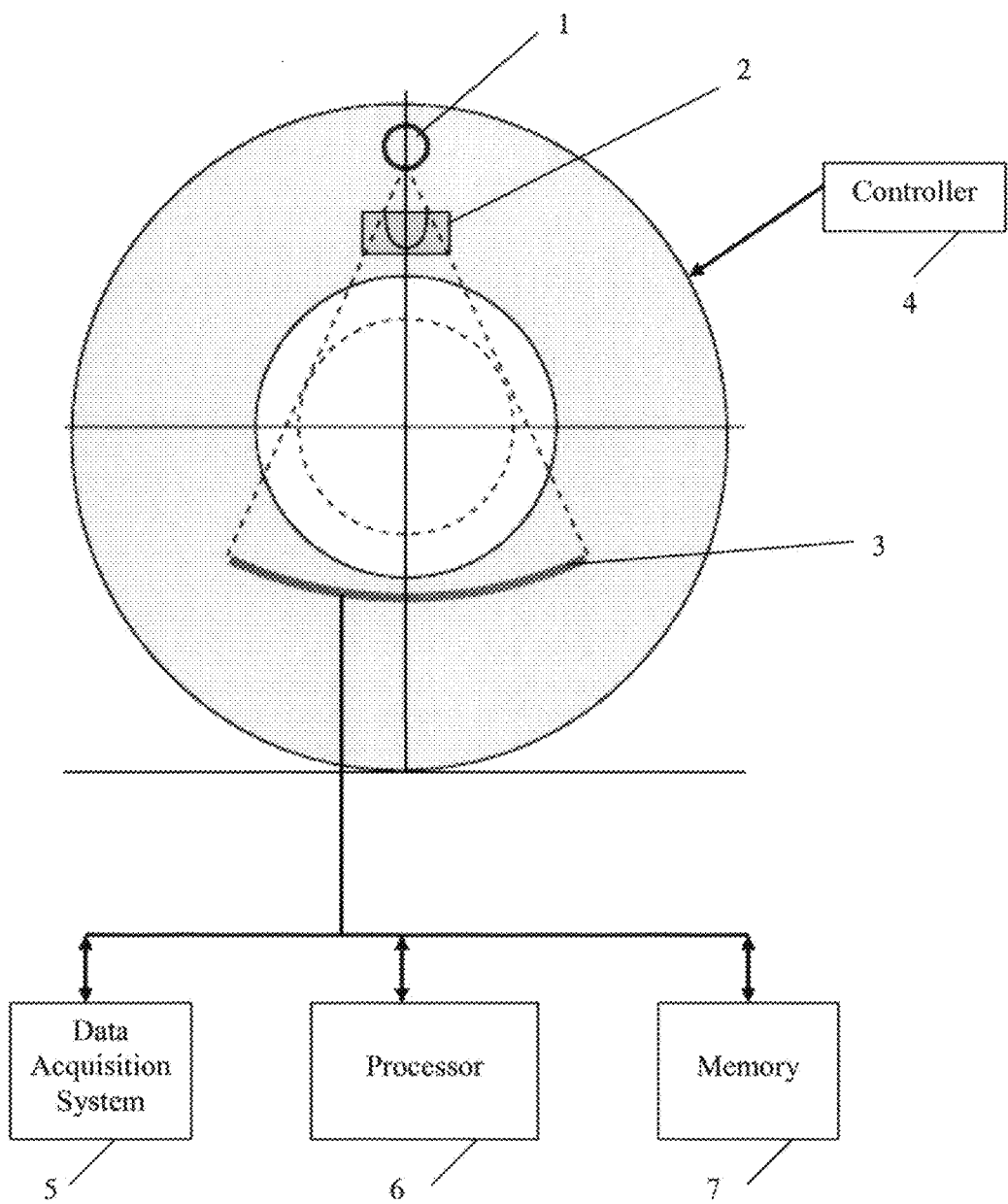
FIG. 17 is a diagram of a mechanically simplified CT apparatus.

FIG. 17 illustrates the basic structure of a CT apparatus that can include the detectors described herein. The CT apparatus of FIG. 17 includes an X-ray tube 1, filters and collimators 2, and detector 3. The CT apparatus will also include additional mechanical and electrical components such as a gantry motor and a controller 4 to control the rotation of the gantry, control the X-ray source, and control a patient bed. The CT apparatus also includes a data acquisition system 5 and a (reconstruction) processor 6 to generate CT images based on the projection data acquired by the data acquisition system. The reconstruction processor makes use of a "map" of the detector that indicates which detector elements are collimated (e.g., tunnels) and which are not. The processor and data acquisition system make use of a memory 7, which is configured to store e.g., data obtained from the detector, the map of the detector, and reconstructed images.

In one embodiment, the reconstruction processor includes a pre-reconstruction processor configured to determine the total, primary, and scatter intensities using the algorithms discussed above. For example, in one embodiment the pre-reconstruction processor is configured to estimate, for each element of the sparse detector elements, a total intensity at the element by averaging intensity values at neighboring elements, and to determine a scatter intensity at the element by subtracting a measured intensity at the element from the estimated total intensity at the element.

The CT apparatus includes the processor 6, which can include the reconstruction processor, that also executes software to determine the waveform parameters of the fast kV switching source according to the algorithm described above with respect to FIG. 19. The processor is configured to obtain energy data from the energy-discriminating detector elements via the data acquisition system to perform the determination. Note that the determination of the waveform parameters can be performed with a detector having sparsely collimated photon-counting detector elements as well as with a detector that does not have sparse collimators.

In one embodiment, the data acquisition system 5 of the CT apparatus includes a first data acquisition system configured to collect information regarding received incident X-ray photons at a first plurality of non-collimated detector elements using a first predetermined sample time interval, and a second data acquisition system configured to collect information regarding received incident X-ray photons at a second plurality of collimated detector elements using a second predetermined sample time interval different from the first predetermined sample time interval.

As one of ordinary skill in the art would recognize, the processor 6 can include a CPU that can be implemented as discrete logic gates, as an Application Specific Integrated Circuit (ASIC), a Field Programmable Gate Array (FPGA) or other Complex Programmable Logic Device (CPLD). An FPGA or CPLD implementation may be coded in VHDL, Verilog, or any other hardware description language and the code may be stored in an electronic memory directly within the FPGA or CPLD, or as a separate electronic memory. Further, the memory may be non-volatile, such as ROM, EPROM, EEPROM or FLASH memory. The memory can also be volatile, such as static or dynamic RAM, and a processor, such as a microcontroller or microprocessor, may be provided to manage the electronic memory as well as the interaction between the FPGA or CPLD and the memory.

Alternatively, the CPU in the reconstruction processor may execute a computer program including a set of computer-readable instructions that perform the functions described herein, the program being stored in any of the above-described non-transitory electronic memories and/or a hard disk drive, CD, DVD, FLASH drive or any other known storage media. Further, the computer-readable instructions may be provided as a utility application, background daemon, or component of an operating system, or combination thereof, executing in conjunction with a processor, such as a Xenon processor from Intel of America or an Opteron processor from AMD of America and an operating system, such as Microsoft VISTA, UNIX, Solaris, LINUX, Apple, MAC-OS and other operating systems known to those skilled in the art.

Once processed by the pre-reconstruction processor, the processed signals are passed to the reconstruction processor, which is configured to generate CT images. The images are stored in the memory, and/or displayed on a display. As one of ordinary skill in the art would recognize, memory can be a hard disk drive, CD-ROM drive, DVD drive, FLASH drive, RAM, ROM or any other electronic storage known in the art. The display can be implemented as an LCD display, CRT display, plasma display, OLED, LED or any other display known in the art. As such, the descriptions of the memory and the display provided herein are merely exemplary and in no way limit the scope of the present advancements.

While certain embodiments have been described, these embodiments have been presented by way of example only, and are not intended to limit the scope of the inventions. Indeed the novel methods and systems described herein may be embodied in a variety of other forms; furthermore, various omissions, substitutions, and changes in the form of the methods and systems described herein may be made without departing from the spirit of the inventions. The accompanying claims and their equivalents are intended to cover such forms or modifications as would fall within the scope and spirit of the inventions.

The invention claimed is:

1. A computed-tomography (CT) detector covering respective angle ranges in the axial and transaxial planes of a CT scanner having an X-ray source, the CT detector comprising:
a plurality of detector elements disposed on a surface to capture incident X-ray photons emitted from the X-ray source; and
a plurality of collimators being smaller in number than the plurality of detector elements, the plurality of collimators being sparsely disposed on the surface, wherein each collimator is associated with and collimates one and only one detector element of the plurality of detector elements and has a height determining a small angle range around a line connecting the X-ray source and a center of the surface of the one detector element so as to allow only X-ray photons originating in the small angle range to reach the one detector.

2. The CT detector of claim 1, wherein each of the detector elements associated with and collimated by one of the plurality of collimators is an energy-discriminating detector element.

3. A computed-tomography (CT) apparatus, comprising:
a CT scanner including a fast kV-switching X-ray source having an uncertain voltage waveform and an uncertain current waveform;
a detector covering respective angle ranges in axial and transaxial planes of the CT scanner, the CT detector including a plurality of energy-discriminating detector elements; and
a processor configured to estimate parameters defining both the voltage waveform and the current waveform based on data acquired from the plurality of energy-discriminating detector elements and a spectrum model.

4. The CT apparatus of claim 3, wherein the processor is configured to:
determine an initial estimate for the parameters,
define a cost function that is based on (1) measured photon numbers for a plurality of energy bins, which are obtained from the data acquired from the plurality of energy-discriminating detector elements, and (2) calculated photon numbers that are calculated based on the spectrum model and linear attenuation coefficients,
calculate partial derivatives of the cost function with respect to each of the parameters, and
determine an updated estimate for the parameters based on the calculated partial derivatives of the cost function.

5. The CT apparatus of claim 4, wherein the processor is further configured to:
determine a difference between the updated estimate for the parameters and the initial estimate for the parameters,
determine whether the determined difference between the updated estimate and the initial estimate is less than a predetermined threshold, and
repeat the steps of calculating the partial derivatives of the cost function, determining an updated estimate for the parameters, and determining a difference between the updated estimate and a previous estimate until the determined difference is less than the predetermined threshold.

6. A method of determining a voltage waveform and a current waveform for a CT apparatus having a CT scanner including a fast kV-switching X-ray source, and a detector including a plurality of energy-discriminating detector elements, the method comprising:
acquiring data from the plurality of energy-discriminating detector elements; and
estimating parameters defining both the voltage waveform and the current waveform based on the acquired data and a spectrum model, wherein the estimating step includes determining an initial estimate for the parameters,
defining a cost function that is based on (1) measured photon numbers for a plurality of energy bins, which are obtained from the data acquired from the plurality of energy-discriminating detector elements, and (2) calculated photon numbers that are calculated based on the spectrum model and linear attenuation coefficients,
calculating partial derivatives of the cost function with respect to each of the parameters, and determining an updated estimate for the parameters based on the calculated partial derivatives of the cost function.

7. The method of claim 6, wherein the estimating step further comprises:
   determining a difference between the updated estimate for the parameters and the initial estimate for the parameters;
   determining whether the determined difference between the updated estimate and the initial estimate is less than a predetermined threshold; and
   repeating the steps of calculating the partial derivatives of the cost function, determining an updated estimate for the parameters, and determining a difference between the updated estimate and a previous estimate until the determined difference is less than the predetermined threshold.

8. A computed-tomography (CT) detector covering respective angle ranges in the axial and transaxial planes of a CT scanner having an X-ray source, the CT detector comprising:
   a plurality of detector elements disposed on a surface to capture incident X-ray photons emitted from the X-ray source, the detector elements being arrayed in slice and rotation directions, the rotation direction being perpendicular to the axial plane of the CT scanner; and
   a plurality of collimators being smaller in number than the plurality of detector elements, the plurality of collimators being sparsely disposed on the surface, wherein each collimator is associated with one detector element of the plurality of detector elements so that the detector elements that are collimated in a given detector row, which extends in the rotation direction, are sparsely located in the given detector row, and
   each collimator has a height determining a small angle range around a line connecting the X-ray source and a center of the surface of the one detector element so as to allow only X-ray photons originating in the small angle range to reach the one detector.

* * * * *